US012612635B2

(12) United States Patent
Zhen et al.

(10) Patent No.: US 12,612,635 B2
(45) Date of Patent: Apr. 28, 2026

(54) BCMA-BINDING SINGLE VARIABLE STRUCTURAL DOMAIN AND ANTIGEN-BINDING MOLECULE

(71) Applicant: CHIA TAI TIANQING PHARMACEUTICAL GROUP CO., LTD., Lianyungang (CN)

(72) Inventors: Zipeng Zhen, Nanjing (CN); Meijuan Xie, Nanjing (CN); Xiuzhen Du, Nanjing (CN); Yimin Ma, Nanjing (CN); Bing Zhang, Nanjing (CN); Tongjie Xu, Nanjing (CN); Xiquan Zhang, Nanjing (CN)

(73) Assignee: CHIA TAI TIANQING PHARMACEUTICAL GROUP CO., LTD., Lianyungang (CN)

( * ) Notice: Subject to any disclaimer, the term of this patent is extended or adjusted under 35 U.S.C. 154(b) by 591 days.

(21) Appl. No.: 18/020,578

(22) PCT Filed: Aug. 16, 2021

(86) PCT No.: PCT/CN2021/112756
§ 371 (c)(1),
(2) Date: Feb. 9, 2023

(87) PCT Pub. No.: WO2022/037527
PCT Pub. Date: Feb. 24, 2022

(65) Prior Publication Data
US 2023/0193292 A1     Jun. 22, 2023

(30) Foreign Application Priority Data
Aug. 20, 2020     (CN) ......................... 202010842370.5

(51) Int. Cl.
| | |
|---|---|
| *C07K 16/28* | (2006.01) |
| *A61K 35/17* | (2015.01) |
| *C07K 19/00* | (2006.01) |
| *C12N 15/62* | (2006.01) |

(52) U.S. Cl.
CPC ............. *C12N 15/62* (2013.01); *A61K 35/17* (2013.01); *C07K 16/28* (2013.01); *C07K 19/00* (2013.01)

(58) Field of Classification Search
None
See application file for complete search history.

(56) References Cited

U.S. PATENT DOCUMENTS

| | | | |
|---|---|---|---|
| 11,447,559 B2 | 9/2022 | Choi et al. | |
| 2003/0012783 A1* | 1/2003 | Kindsvogel | ............. A61P 31/00 |
| | | | 424/178.1 |
| 2013/0156770 A1* | 6/2013 | Kufer | ........................ A61P 7/00 |
| | | | 435/69.6 |
| 2013/0273055 A1* | 10/2013 | Borges | .................... A61P 37/02 |
| | | | 530/387.3 |
| 2014/0161828 A1* | 6/2014 | Armitage | ............. A61K 31/395 |
| | | | 435/69.6 |
| 2016/0297884 A1* | 10/2016 | Kuo | ................... C07K 14/7051 |
| 2017/0166649 A1* | 6/2017 | Oden | ................. A61K 47/6867 |
| 2020/0299395 A1 | 9/2020 | Choi et al. | |
| 2022/0251226 A1 | 8/2022 | Zhang et al. | |

FOREIGN PATENT DOCUMENTS

| | | |
|---|---|---|
| CN | 109942708 A | 6/2019 |
| CN | 109942709 A | 6/2019 |
| CN | 111201243 A | 5/2020 |
| CN | 111333729 A | 6/2020 |
| CN | 111542343 A | 8/2020 |
| WO | 2019/229701 A2 | 12/2019 |
| WO | 2020/038147 A1 | 2/2020 |
| WO | 2022/218380 A1 | 10/2022 |

OTHER PUBLICATIONS

Janeway et al., Immunobiology, 3rd edition, 1997, Garland Publishing Inc., pp. 3:1-3:11.*
Rudikoff et al., Proc Natl Acad Sci USA. Mar. 1982;79(6):1979-83.*
Edwards et al.,J Mol Biol. Nov. 14, 2003;334(1): 103-18.*
Llyod et al., Protein Eng Des Sel. Mar. 2009;22(3):159-68. doi: 10.1093/protein/gzn058. Epub Oct. 29, 2008.*
Goel et al., J Immunol. Dec. 15, 2004; 173(12):7358-67.*
Ghahroudi et al., FEBS Letters Sep. 15, 1997; 414(3): 521-526.*
Nov. 2, 2021 International Search Report issued in International Patent Application No. PCT/CN2021/112756.
Wen WU et al.; "A Novel VHH Antibody Targeting the B Cell-Activating Factor for B-Cell Lymphoma"; International Journal of Molecular Sciences; 2014; vol. 15; pp. 9481-9496.

* cited by examiner

*Primary Examiner* — Michael Szperka
(74) *Attorney, Agent, or Firm* — Oliff PLC

(57) ABSTRACT

A BCMA-binding immunoglobulin single variable structural domain and an antigen-binding molecule including an immunoglobulin single variable structural domain and an antigen-binding molecule, a nucleic acid encoding the above, a vector containing the nucleic acid, a cell containing the vector, and a pharmaceutical composition containing the above, as well as a therapeutic use thereof.

16 Claims, 4 Drawing Sheets

Specification includes a Sequence Listing.

CHO-hBCMA

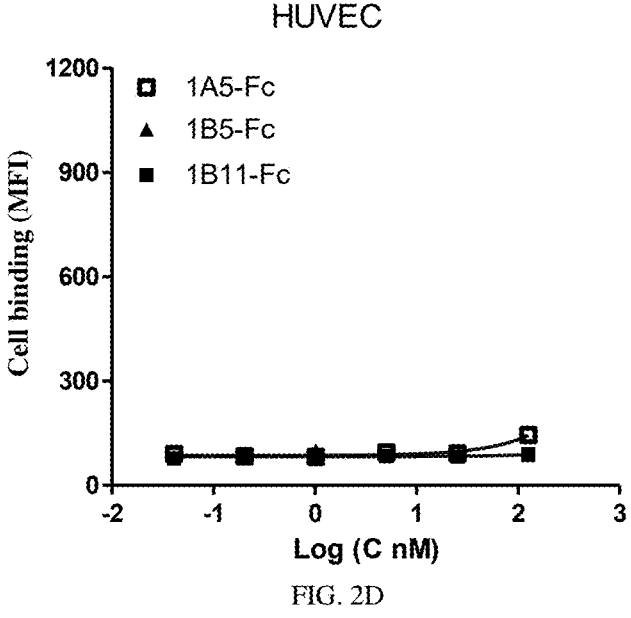
FIG. 2D
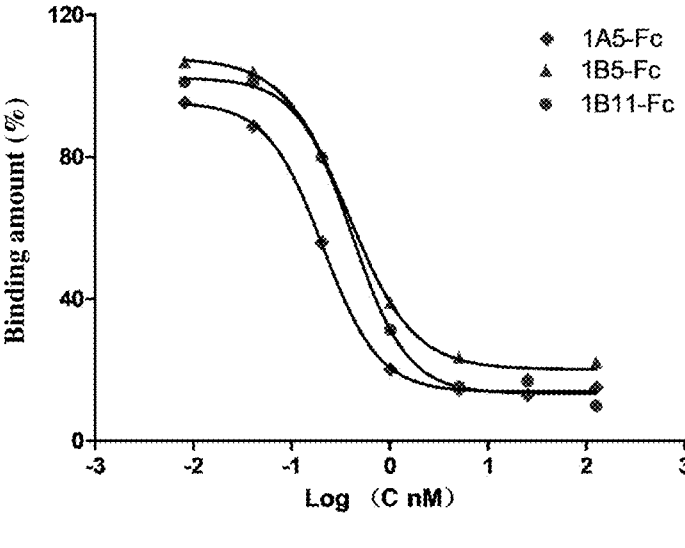
FIG. 3
Hu-BCMA-ECD
FIG. 4A

BCMA-BINDING SINGLE VARIABLE STRUCTURAL DOMAIN AND ANTIGEN-BINDING MOLECULE

TECHNICAL FIELD

The present invention relates to an antigen-binding molecule, and in particular to a BCMA-binding single variable domain and an antigen-binding molecule.

BACKGROUND

B-cell maturation antigen (BCMA), also known as tumor necrosis factor receptor superfamily member 17 (TN-FRS17), is a protein that in humans is encoded by the TNFRSF17 gene. BAFF and APRIL are ligands for BCMA. BAFF (also known as BLyS, TALL-1, THANK, zTNF4, TNFSF20 or D8Ertd387e) is a high-affinity ligand for BCMA. APRIL (A proliferation-inducing ligand, also known as TNFSF13, TALL-2 or TRDL-1) is a low-affinity ligand for BCMA. In addition, BAFF and APRIL are also ligands for tumor necrosis factor receptor (TNFR) super-family member B-cell activation factor receptor (BAFF-R), and for transmembrane activator and calcium modulator and cyclophilin ligand interactor (TACI). BCMA together with BAFF-R and TACI regulates the proliferation, survival, maturation and differentiation of B cells.

Multiple myeloma is a malignant disease of plasma cells. In cells of multiple myeloma, the BCMA expression level is significantly increased. BCMA can be a suitable tumor antigen target for immunotherapeutic agents for multiple myeloma. Immunotherapeutic agents such as antibodies that bind to BCMA are able to block the binding of BCMA to its natural ligand BAFF or/and APRIL. With BCMA being a potential therapeutic target, some BCMA-targeting antibodies have been developed, but still are limited. There is a need for more available options. In addition to conventional IgG1 antibodies of a four-chain structure comprising light chains and heavy chains, IgG antibodies in animals of the family Camelidae also include naturally occurring IgG2 and IgG3 heavy-chain antibodies (HcAbs) free of light chains. The single variable region domains ($V_HH$s or single variable domains) of heavy-chain antibodies have the characteristics of specifically binding to antigens and have relatively high affinity for antigens. They are called single-domain antibodies (sdAbs). Based on their uniqueness, $V_HH$s domains used alone or as part of a larger antigen-binding molecule have more significant advantages over conventional scFvs and antibody fragments such as Fabs: for example, only a single domain is required to specifically bind to an antigen with high affinity; they can be easily transformed into polyvalent and multispecific formats; $V_HH$ domains are highly soluble and do not tend to aggregate; the molecules are small and thus demonstrate relatively high tissue permeability; single-domain antibodies do not need to be paired with light chains, and thus there is no light and heavy chain mismatch problem about forming bispecific or multispecific antibodies, and the like.

SUMMARY

The present invention provides a BCMA-binding single variable domain and an antigen-binding molecule. The present invention also provides related nucleotides that can encode the provided single variable domain and antigen-binding molecule, a vector, a cell, a composition, a method of construction, and use.

In one aspect, the present invention provides an isolated single variable domain that binds to BCMA, wherein the single variable domain comprises CDR1, CDR2 and CDR3 selected from the group consisting of:
- (a) CDR1 having at least 70% sequence identity to an amino acid sequence selected from the group consisting of SEQ ID NOs: 7, 10 and 13;
- (b) CDR2 having at least 85% sequence identity to an amino acid sequence selected from the group consisting of SEQ ID NOs: 8, 11 and 14; and
- (c) CDR3 having at least 85% sequence identity to an amino acid sequence selected from the group consisting of SEQ ID NOs: 9, 12 and 15.

In some embodiments, the single variable domain comprises CDR1, CDR2 and CDR3 selected from any one of the following:
- (i) CDR1 comprising an amino acid sequence of SEQ ID NO: 7; CDR2 comprising an amino acid sequence of SEQ ID NO: 8; and CDR3 comprising an amino acid sequence of SEQ ID NO: 9;
- (ii) CDR1 comprising an amino acid sequence of SEQ ID NO: 10; CDR2 comprising an amino acid sequence of SEQ ID NO: 11; and CDR3 comprising an amino acid sequence of SEQ ID NO: 12; and
- (iii) CDR1 comprising an amino acid sequence of SEQ ID NO: 13; CDR2 comprising an amino acid sequence of SEQ ID NO: 14; and CDR3 comprising an amino acid sequence of SEQ ID NO: 15.

In some embodiments, the single variable domain comprises an amino acid sequence having any one of at least 85%, 86%, 87%, 88%, 89%, 90%, 91%, 92%, 93%, 94%, 95%, 96%, 97%, 98%, 99% and 100% sequence identity to a sequence of SEQ ID NO: 16, 18 or 20.

In one aspect, the present invention provides an isolated single variable domain, wherein the single variable domain comprises CDR1, CDR2 and CDR3 of an amino acid sequence of SEQ ID NO: 16, 18 or 20.

In one aspect, the present invention provides an isolated single variable domain, wherein the single variable domain comprises an amino acid sequence of SEQ ID NO: 16, 18 or 20.

In one aspect, the present invention provides an isolated single variable domain that binds to a BCMA extracellular region. The binding site is located at one or more amino acids at positions Ser9-Pro23 in the BCMA extracellular region. The amino acid sequence of the BCMA extracellular region is set forth in SEQ ID NO: 6. The positions are numbered in sequence, starting with the first amino acid (position 1) of the BCMA extracellular region.

In one aspect, the present invention provides an isolated single variable domain, wherein the single variable domain binds to the same epitopes as the single variable domain described in any one of the embodiments herein.

In one aspect, the present invention provides an isolated single variable domain, wherein the single variable domain competes for binding to BCMA with the single variable domain described in any one of the embodiments herein.

In some embodiments, the single variable domain described herein above is derived from animals of the family Camelidae or is humanized. In some embodiments, the single variable domain described herein above is a $V_HH$, preferably a camelid or humanized $V_HH$.

In one aspect, the present invention provides use of the single variable domain described herein, including use for constructing an antigen-binding molecule, preferably an antibody, a monospecific antibody, a multispecific antibody or an immunoconjugate.

In one aspect, the present invention provides an isolated antigen-binding molecule that binds to BCMA and that comprises at least one single variable domain described herein. In some embodiments, the antigen-binding molecule comprises an amino acid sequence set forth in SEQ ID NO: 22, 24 or 26.

In one aspect, the present invention provides a composition comprising an active ingredient and a pharmaceutically acceptable carrier, wherein the active ingredient is the single variable domain described herein or the antigen-binding molecule described herein.

In one aspect, the present invention provides an isolated nucleic acid encoding the single variable domain described herein or the antigen-binding molecule described herein.

In one aspect, the present invention provides a vector comprising the isolated nucleic acid described herein.

In one aspect, the present invention provides a host cell comprising the vector described herein.

In one aspect, the present invention provides a method for detecting or measuring BCMA in a sample, which comprises contacting the sample with the single variable domain described herein or the antigen-binding molecule described herein and detecting or measuring a binding complex.

In one aspect, the present invention provides a method for preparing the single variable domain described herein, which comprises: culturing the host cell and isolating the single variable domain expressed, wherein the vector is an expression vector; the host cell comprises a nucleic acid encoding the single variable domain.

In one aspect, the present invention provides a method for preparing the antigen-binding molecule, which comprises: culturing the host cell and isolating the antigen-binding molecule expressed, wherein the vector is an expression vector; the host cell comprises a nucleic acid encoding the antigen-binding molecule.

In another aspect, the present invention provides a method for treating a subject with a BCMA-expressing tumor, which comprises administering to the subject a therapeutically effective amount of the single variable domain, the antigen-binding molecule or the composition.

In another aspect, the present invention provides a method for inhibiting, reducing or blocking BCMA signaling in a cell, which comprises administering to the cell an effective amount of the single variable domain, the antigen-binding molecule or the composition.

In another aspect, the present invention provides a method for killing BCMA-expressing tumor cells or inhibiting growth of BCMA-expressing tumor cells, which comprises contacting the tumor cells with the single variable domain, the antigen-binding molecule or the composition.

In another aspect, the present invention provides a method for treating a subject with an autoimmune disease, which comprises administering to the subject a therapeutically effective amount of the single variable domain described herein, the antigen-binding molecule described herein or the composition described herein.

4

Figure 2A:
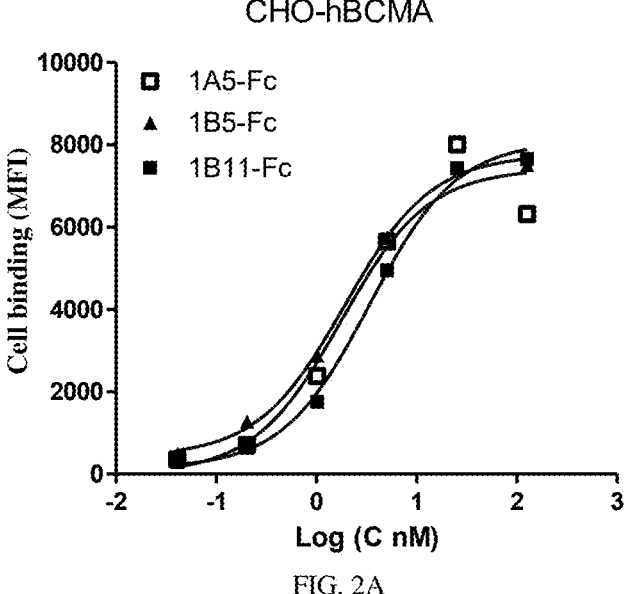
FIG. 2A shows curves of flow cytometry assays for binding of anti-human BCMA VHH-Fc chimeric antibodies to CHO-hBCMA cells.
Figure 2B:
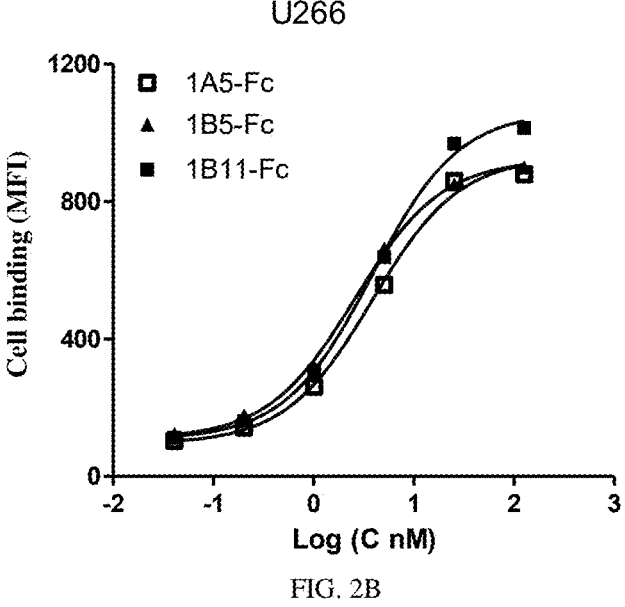

FIG. 2B shows curves of flow cytometry assays for binding of anti-human BCMA VHH-Fc chimeric antibodies to U266 cells.

Figure 2C:
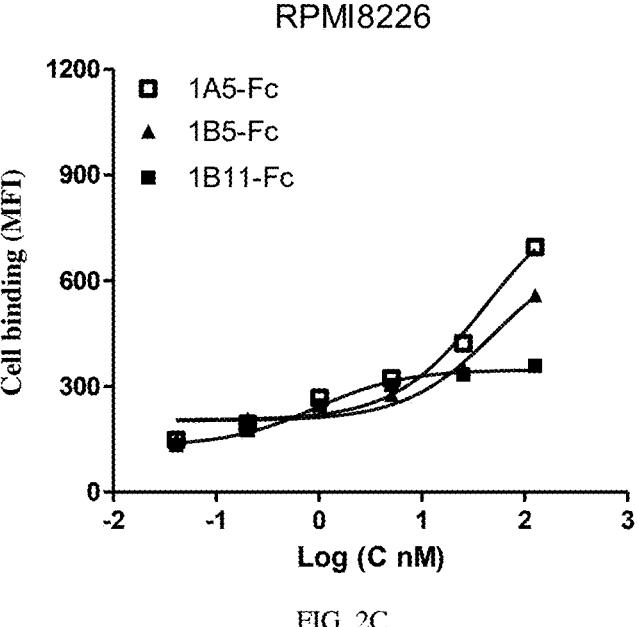

FIG. 2C shows curves of flow cytometry assays for binding of anti-human BCMA VHH-Fc chimeric antibodies to RPMI8226 cells.

FIG. 2D shows curves of flow cytometry assays for binding of anti-human BCMA VHH-Fc chimeric antibodies to HUVEC cells.

FIG. 3 shows the results of competitive ELISA assays for human BCMA VHH-Fc chimeric antibody and ligand APRIL.

FIG. 4A shows the amino acid sequence of the extracellular region of human BCMA.

Figure 4B:
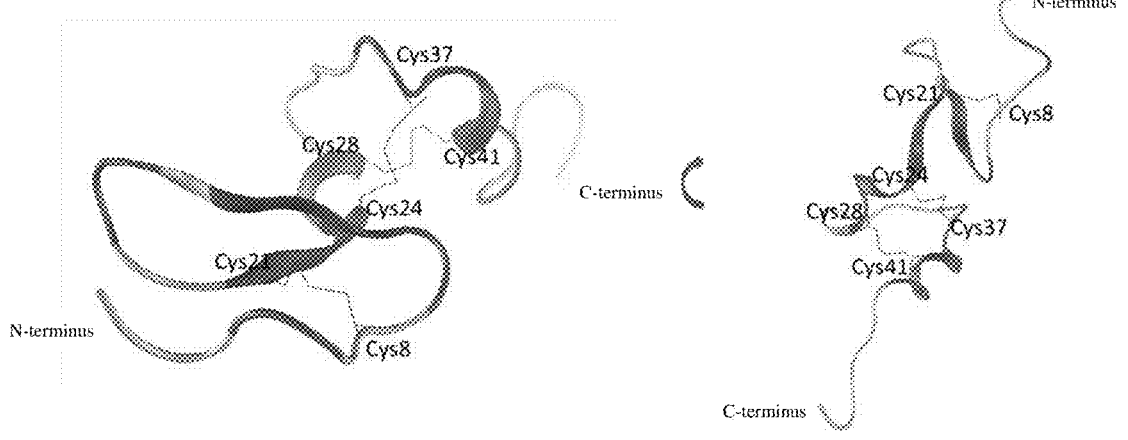

FIG. 4B shows the crystal structure of the extracellular region of human BCMA.

Figure 4C:
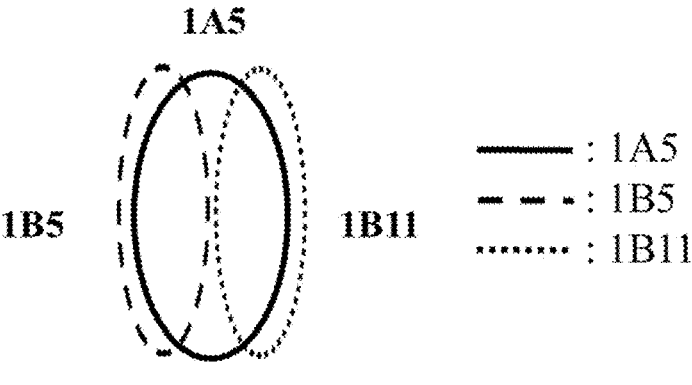

FIG. 4C shows the epitope relationship of 1A5, 1B5 and 1B11.

DETAILED DESCRIPTION

Terminology

The term "antigen-binding molecule" in its broadest sense refers to a molecule that specifically binds to an antigenic determinant. Some examples of antigen-binding molecule are antibodies, fusion proteins or antibody conjugates.

The term "immunoglobulin" refers to a protein having the structure of a naturally occurring antibody. For example, human IgG immunoglobulins are heterotetrameric glycoproteins of about 150,000 daltons, composed of two light chains and two heavy chains linked by disulfide bonds. From N-terminus to C-terminus, each heavy chain has a heavy chain variable region (VH) followed by a hinge region (HR) and three constant domains (CH1, CH2 and CH3), also known as heavy chain constant regions. In the case of IgE immunoglobulins, the heavy chain also has a CH4 domain. Thus, an immunoglobulin heavy chain is a polypeptide consisting of the following domains in the N-terminus to C-terminus direction: VH—CH1-HR—CH2-CH3-(CH4). Similarly, from N-terminus to C-terminus, each light chain has a light chain variable region (VL) followed by a constant light chain domain, also known as a light chain constant region (CL). Thus, an immunoglobulin light chain is a polypeptide consisting of the following domains in the N-terminus to C-terminus direction: VL-CL. Human immunoglobulins essentially consist of two pairs of Fab and Fc domains linked by a hinge region.

The term "antibody" is used in its broadest sense and encompasses a variety of antibody structures including, but not limited to, monoclonal antibodies, polyclonal antibodies, multispecific antibodies (e.g., bispecific antibodies and trispecific antibodies) and antibody fragments, so long as they exhibit the desired antigen-binding activity.

The term "variable domain" or "variable region" refers to a domain of an antibody that is involved in the binding of the antibody to an antigen. Each variable domain of a natural antibody consists essentially of four "framework regions" and three complementarity-determining regions. The four "framework regions" are referred to in the art and hereinafter as "framework region 1" or "FR1", "framework region 2" or "FR2", "framework region 3" or "FR3", and "framework region 4" or "FR4". The framework regions are separated by three "complementarity-determining regions" or "CDRs" referred to in the art and hereinafter as "complementarity-determining region 1" or "CDR1", "complementarity-determining region 2" or "CDR2", and "complementarity-determining region 3" or "CDR3". Thus, the general structure or sequence of a variable domain can be represented as follows: FR1-CDR1-FR2-CDR2-FR3-CDR3-FR4. Variable domains impart specificity for an antigen to an antibody by virtue of having an antigen-binding site.

The term "single variable domain" refers to a variable domain capable of specifically binding to an antigen epitope without being paired with other variable domains. The antigen-binding site of a single variable domain is typically formed from three CDRs (CDR1, CDR2 and CDR3) and present on a single domain. In some cases, a single variable domain may be a heavy chain variable domain (e.g. VH) or a suitable fragment thereof, so long as it can form a single antigen-binding unit (i.e., a functional antigen-binding unit consisting essentially of a single variable domain; in this way, a single antigen-binding domain can form a functional antigen-binding unit without interacting with another variable domain). Another example of single variable domain is "VHH domain" (or simply "VHH" or "$V_HH$") of the family Camelidae.

"VHH domain", also known as VHH, $V_HH$ or $V_HH$ domain or single-domain antibody, was originally described as the antigen-binding variable domain of "heavy-chain antibody" (i.e., "antibodies lacking light chains"). The term "VHH domain" is used to distinguish these variable domains from the heavy chain variable domains present in conventional four-chain antibodies (which are referred to herein as "VH domains" or "VHs") and the light chain variable domains present in conventional four-chain antibodies (which are referred to herein as "VL domains" or "VLs"). VHH domains specifically bind to epitopes without additional antigen-binding domains involved (it is different with the VH or VL domains of conventional four-chain antibodies—in this case epitopes are recognized by both the VL and VH domains). VHH domains are small, stable and efficient antigen recognition units formed from a single domain.

"CDR" (complementarity-determining region), also known as "hypervariable region (HVR)", typically refers to each region of antibody variable regions which are highly variable in sequence and/or form structurally defined loops. Natural four-chain antibodies typically comprise six CDRs, three in the heavy chain variable region (heavy chain CDR1, heavy chain CDR2, and heavy chain CDR3) and three in the light chain variable region (light chain CDR1, light chain CDR2, and light chain CDR3). Heavy-chain antibodies or single variable domains typically have three CDRs (CDR1 (or HVR1), CDR2 (or HVR2), and CDR3 (or HVR3)). CDR3 appears to be the most diverse of the three CDRs and is believed to play a unique role in imparting fine specificity to antibodies.

There are currently many ways to define CDRs. The Kabat scheme defines CDRs based on sequence variability and is the most commonly used (Elvin A. Kabat, et al, *Sequences of Proteins of Immunological Interest*, 5th Edition, Public Health Service, National Institutes of Health, Bethesda, Md. (1991)), while the Chothia scheme defines CDRs based on the position of structural loops (Cyrus Chothia, et al, Canonical Structures for the Hypervariable Regions of Immunoglobulins, *J. Mol. Biol.* 196:901-917 (1987)). The AbM scheme, a compromise between the Kabat scheme and the Chothia scheme, is used by the Oxford Molecular's AbM antibody modeling software. "Contact" defines CDRs based on the analysis of the crystal structure of available complexes. The residues for each of these CDRs are recorded in Table S1 below.

TABLE S1

| | | CDR definitions | | |
|---|---|---|---|---|
| CDR | Kabat | AbM | Chothia | Contact |
| VL CDR1 | L24-L34 | L24-L34 | L26-L32 | L30-L36 |
| VL CDR2 | L50-L56 | L50-L56 | L50-L52 | L46-L55 |
| VL CDR3 | L89-L97 | L89-L97 | L91-L96 | L89-L96 |
| VH CDR1 | H31-H35B | H26-H35B (Kabat numbering) | H26-H32 | H30-H35B |
| VH CDR1 | H31-H35 | H26-H35 (Chothia numbering) | H26-H32 | H30-H35 |
| VH CDR2 | H50-H65 | H50-H58 | H53-H55 | H47-H58 |
| VH CDR3 | H95-H102 | H95-H102 | H96-H101 | H93-H101 |

In certain specific contexts herein, "complementarity-determining region", "CDR" or "HVR" is used to refer to Kabat-defined CDRs (Elvin A. Kabat, et al, *Sequences of Proteins of Immunological Interest*, 5th Edition, Public Health Service, National Institutes of Health, Bethesda, Md. (1991)). Based on the amino acid sequences of the variable regions of an antibody, those skilled in the art can routinely determine which amino acid residues a CDR defined by any scheme contains, and other CDRs defined by any scheme (e.g., defined by the Chothia or AbM scheme) are also encompassed within the scope of the present invention.

Amino acid residues of single variable domains (such as $V_HH$) are numbered according to the general numbering system for VH given by Kabat et al. (Elvin A. Kabat, et al, *Sequences of Proteins of Immunological Interest*, 5th Edition, Public Health Service, National Institutes of Health, Bethesda, Md. (1991)) as was applied to the camelid $V_HH$ domains in L Riechmann, et al, Single domain antibodies: comparison of camel VH and camelised human VH domains, *J. Immunol. Methods* (1999). According to the numbering, FR1 of the $V_HH$ comprises amino acid residues at positions 1-30; CDR1 of the $V_HH$ comprises amino acid residues at positions 31-35; FR2 of the $V_HH$ comprises amino acids at positions 36-49; CDR2 of the $V_HH$ comprises amino acid residues at positions 50-65; FR3 of the $V_HH$ comprises amino acid residues at positions 66-94; CDR3 of the $V_HH$ comprises amino acid residues at positions 95-102; FR4 of the $V_HH$ comprises amino acid residues at position 103-113. In this regard, it should be noted that, as is well known in the art for VH and $V_HH$, the total number of amino acid residues in each CDR may vary and may not correspond to the total number of amino acid residues indicated by Kabat numbering (that is, one or more positions according to Kabat numbering may not be occupied in actual sequences, or actual sequence may contain more amino acid residues than Kabat numbering allows).

"Variable domain residue numbering as in Kabat" or "amino acid position numbering as in Kabat" and variations thereof refer to the numbering system used by Kabat et al. (Elvin A. Kabat, et al, *Sequences of Proteins of Immunological Interest*, 5th Edition, Public Health Service, National Institutes of Health, Bethesda, Md. (1991)) to encode the heavy chain variable domain or the light chain variable domain of an antibody. With the numbering system, an actual linear amino acid sequence may contain fewer or additional amino acids corresponding to shortening or insertion of FRs or CDRs of a variable domain. For example, a heavy chain variable domain may include a single amino acid insert (amino acid residue 52a according to Kabat) following amino acid residue 52 of CDR2 and inserted amino acid residues (e.g., amino acid residues 82a, 82b and 82c and the like according to Kabat) following amino acid residue 82 of heavy chain FR. For a given antibody, the Kabat numbering of amino acid residues can be determined by aligning the antibody sequence to a homologous region sequence of "standard" Kabat numbering.

The term "framework region" or "FR" residues are amino acid residues of variable domains other than the CDR residues defined herein.

The term "human consensus framework" or "acceptor human framework" refers to a framework of the most frequently occurring amino acid residues in selecting human immunoglobulin VL or VH framework sequences. In general, human immunoglobulin VL or VH sequences is selected from a subgroup of variable domain sequences. In general, the subgroup of sequences is that in Kabat et al, *Sequences of Proteins of Immunological Interest,* 5th Edition, Public Health Service, National Institutes of Health, Bethesda, Md. (1991). Examples include: for VL, the subgroup may be subgroup κI, κII, κIII or κIV described by Kabat et al. (from the same source as is described above). In addition, for VH, the subgroup may be subgroup I, subgroup II or subgroup III described by Kabat et al. Alternatively, the human consensus framework region may be derived from particular residues described above; for example, when human framework residues are selected according to the homology of human framework region residues to a donor framework region by aligning the donor framework region sequence to a set of various human framework region sequences, the acceptor human framework "derived from" the human consensus framework region may comprise the same amino acid sequence, or it may comprise pre-existing amino acid sequence variations. In some embodiments, the number of pre-existing amino acid changes is 10 or less, 9 or less, 8 or less, 7 or less, 6 or less, 5 or less, 4 or less, 3 or less, or 2 or less.

The term "Fc domain" or "Fc" is used to define the C-terminal region of an immunoglobulin heavy chain, which comprises at least part of a constant region. The term includes natural sequence Fc and variant Fc. The C-terminal lysine of Fc (Lys447 according to the EU numbering system) may be present or not.

The term "$EC_{50}$" refers to the effective concentration, 50% of the maximal response of an antigen-binding molecule. The term "$IC_{50}$" refers to the inhibitory concentration, 50% of the maximal response of an antigen-binding molecule. Both $EC_{50}$ and $IC_{50}$ can be measured by ELISA or FACS assay or any other method known in the art.

The term "KD" as used herein refers to the equilibrium dissociation constant, expressed in molar concentration (M). The KD value of an antigen-binding molecule can be determined using methods well known in the art. A method of determining the KD value of an antigen-binding molecule is to use surface plasmon resonance, e.g., to use a biosensor system, such as a Biacore system.

The term "treatment" refers to a measure taken to statistically significantly treat, cure, alleviate, relieve, alter, remedy, ameliorate, improve or affect an illness (e.g., a disease) and a symptom of the illness, or prevent or delay the onset of the symptom, a complication and biochemical indicators, or otherwise prevent or inhibit the further progression of the disease, illness or disorder.

The term "therapeutically effective amount" refers to the amount of an antigen-binding molecule or a composition or other applicants necessary to provide a therapeutic and/or prophylactic benefit to a subject.

The term "subject" includes any human or non-human animal. The term "non-human animal" includes all vertebrates, e.g., mammals and non-mammals, such as non-human primates, sheep, dog, cat, horse, cow, chicken, amphibians, and reptiles. Preferably, the subject according to the present invention is a human. The terms "patient" and "subject" are used interchangeably unless otherwise indicated.

The term "specific binding" or "specifically bind to" means that the binding is selective for an antigen and can be distinguished from interactions that are not desired or are non-specific. The ability of an antigen-binding molecule or single variable domain to bind to a particular antigenic determinant may be measured by enzyme-linked immunosorbent assay (ELISA) or other techniques familiar to those skilled in the art, e.g., the surface plasmon resonance (SPR) technique (analysis on a Biacore instrument).

The term "isolated" means that a compound of interest (e.g., a VHH, an antigen-binding molecule, an antibody or a nucleic acid) has been isolated from its natural environment.

The term "epitope" or the interchangeably used term "antigenic determinant" refers to any antigenic determinant on an antigen to which the paratope of an antibody binds. Antigenic determinants generally comprise chemically active surface groups of molecules, such as amino acids or sugar side chains, and generally have specific three-dimensional structural characteristics as well as specific charge characteristics. For example, an epitope typically includes at least 3, 4, 5, 6, 7, 8, 9, 10, 11, 12, 13, 14 or 15 contiguous or non-contiguous amino acids in a unique spatial conformation. It may be a "linear" epitope or a "conformational" epitope. In a linear epitope, all the points of interaction between a protein and an interacting molecule (e.g., an antibody) exist linearly along the primary amino acid sequence of the protein. In a conformational epitope, the points of interaction exist across protein amino acid residues that are separated from each other. The term sequence "identity" is also known as homology. The percent identity between two sequences is a function of identical positions shared by the sequences (i.e., % identity=number of identical positions/total number of positions×100), where the number of gaps that need to be introduced to produce an optimal alignment of the two sequences and the length of each gap should be taken into consideration. As shown in the following non-limiting examples, comparison of sequences and determination of percent identity between two sequences can be accomplished using a mathematical algorithm. The percent identity between two amino acid sequences can be determined using the algorithm of E. Meyers and W. Miller (*Comput. Appl. Biosci.,* 4:11-17 (1988)), which has been incorporated into the ALIGN program (version 2.0) and uses a PAM120 residue weight table with a gap length penalty of 12 and a gap penalty of 4. In addition, the percent identity of two amino acid sequences can be determined using the algorithm of Needleman and Wunsch (J. Mol. Biol., 484-453 (1970)), which has been incorporated into the GAP program in the GCG software package (available at www.gcg.com) and uses the Blossum 62 matrix or the PAM250 matrix with a gap weight of 16, 14, 12, 10, 8, 6 or 4 and a length weight of 1, 2, 3, 4, 5 or 6.

As used herein, "about" means being within an acceptable error range determined by those of ordinary skill in the art for a particular value, which will depend in part on how the value is measured or determined, i.e., the limitation by the measurement system. For example, "about" may mean being within 1 or more than 1 standard deviation, as practiced in the art. Alternatively, "about" may mean a range of up to 5% (i.e., ±5%), for example, fluctuating within a particular numerical range given±2%, ±1% or ±0.5%. Furthermore, particularly with respect to biological systems or methods, the term may refer to being up to an order of magnitude or up to 5 times a certain value. When a particular value is given in the present application or in the claims, unless otherwise stated, "about" should be considered to mean being within an acceptable error range for that particular value.

Unless otherwise indicated herein, the term "include" or equivalents thereof (e.g., comprise and contain) is an open-ended term. It means including but not limited to the stated elements, steps or components but is open to the elements, steps or components not explicitly stated.

Unless otherwise stated herein, singular terms encompass plural forms, and vice versa.

All patents, patent applications and other identified publications are expressly incorporated herein by reference for the purpose of description and disclosure. These publications are provided solely because they were disclosed prior to the filing date of the present application. All statements as to the dates of these documents or description as to the contents of these documents are based on the information available to the applicant and do not constitute any admission as to the correctness of the dates or the content of these documents. Moreover, in any country or region, any reference to these publications herein is not to be construed as an admission that the publications form part of the commonly recognized knowledge in the art. Various aspects of the present invention will be described in further detail in the following sections.

Single Variable Domain

One aspect of the present invention provides an isolated single variable domain that binds to BCMA (such as human BCMA). The single variable domain provides more available options for the development or drug construction of BCMA-targeting drugs. The single variable domain has a number of desirable therapeutic properties such as good affinity for human BCMA, and are able to block the binding of the proliferation-inducing ligand APRIL to BCMA. In particular, in some embodiments, the single variable domain does not bind to human TACI and BAFFR proteins, exhibiting specificity.

In some embodiments, provided is a BCMA-binding single variable domain comprising one, two or all three CDRs of a single variable domain set forth in SEQ ID NO: 16. In one specific embodiment, provided is a BCMA-binding single variable domain comprising CDR1, CDR2 and CDR3 of a single variable domain set forth in SEQ ID NO: 16. In some embodiments, provided is a BCMA-binding single variable domain comprising one, two or all three CDRs of a single variable domain set forth in SEQ ID NO: 18. In one specific embodiment, provided is a BCMA-binding single variable domain comprising CDR1, CDR2 and CDR3 of a single variable domain set forth in SEQ ID NO: 18. In some embodiments, provided is a BCMA-binding single variable domain comprising one, two or all three CDRs of a single variable domain set forth in SEQ ID NO: 20. In one specific embodiment, provided is a BCMA-binding single variable domain comprising CDR1, CDR2 and CDR3 of a single variable domain set forth in SEQ ID NO: 20. In some embodiments, the single variable domain is derived from animals of the family Camelidae. In some embodiments, the single variable domain is humanized. In some embodiments, the single variable domain comprises an acceptor human framework.

In some embodiments, provided is a BCMA-binding single variable domain comprising at least one, at least two, or all three CDRs selected from the group consisting of: (a) CDR1 comprising an amino acid sequence selected from the group consisting of SEQ ID NOs: 7, 10 and 13; (b) CDR2 comprising an amino acid sequence selected from the group consisting of SEQ ID NOs: 8, 11 and 14; and (c) CDR3 comprising an amino acid sequence selected from the group consisting of SEQ ID NOs: 9, 12 and 15. In some embodiments, the single variable domain is derived from animals of the family Camelidae. In some embodiments, the single variable domain is humanized. In some embodiments, the single variable domain comprises an acceptor human framework.

In some embodiments, provided is a BCMA-binding single variable domain comprising three CDRs (CDR1, CDR2 and CDR3), including: (a) CDR1 having any one of at least about 70%, about 75%, about 80%, about 85%, about 86%, about 87%, about 88%, about 89%, about 90%, about 91%, about 92%, about 93%, about 94%, about 95%, about 96%, about 97%, about 98%, about 99% and about 100% sequence identity to an amino acid sequence selected from the group consisting of SEQ ID NOs: 7, 10 and 13; (b) CDR2 having any one of at least about 85%, about 86%, about 87%, about 88%, about 89%, about 90%, about 91%, about 92%, about 93%, about 94%, about 95%, about 96%, about 97%, about 98%, about 99% and about 100% sequence identity to an amino acid sequence selected from the group consisting of SEQ ID NOs: 8, 11 and 14; and (c) CDR3 having any one of at least about 85%, about 86%, about 87%, about 88%, about 89%, about 90%, about 91%, about 92%, about 93%, about 94%, about 95%, about 96%, about 97%, about 98%, about 99% and about 100% sequence identity to an amino acid sequence selected from the group consisting of SEQ ID NOs: 9, 12 and 15. In some specific embodiments, provided is a BCMA-binding single variable domain comprising three CDRs (CDR1, CDR2 and CDR3), including: (a) CDR1 having any one of at least about 70%, about 75%, about 80%, about 85%, about 86%, about 87%, about 88%, about 89%, about 90%, about 91%, about 92%, about 93%, about 94%, about 95%, about 96%, about 97%, about 98%, about 99% and about 100% sequence identity to an amino acid sequence of SEQ ID NO: 7; (b) CDR2 having any one of at least about 85%, about 86%, about 87%, about 88%, about 89%, about 90%, about 91%, about 92%, about 93%, about 94%, about 95%, about 96%, about 97%, about 98%, about 99% and about 100% sequence identity to an amino acid sequence of SEQ ID NO: 8; and (c) CDR3 having any one of at least about 85%, about 86%, about 87%, about 88%, about 89%, about 90%, about 91%, about 92%, about 93%, about 94%, about 95%, about 96%, about 97%, about 98%, about 99% and about 100% sequence identity to an amino acid sequence selected of SEQ ID NO: 9. In some specific embodiments, provided is a BCMA-binding single variable domain comprising three CDRs (CDR1, CDR2 and CDR3), including: (a) CDR1 having any one of at least about 70%, about 75%, about 80%, about 85%, about 86%, about 87%, about 88%, about 89%, about 90%, about 91%, about 92%, about 93%, about 94%, about 95%, about 96%, about 97%, about 98%, about 99% and about 100% sequence identity to an amino acid sequence of SEQ ID NO: 10; (b) CDR2 having any one of at least about 85%, about 86%, about 87%, about 88%, about 89%, about 90%, about 91%, about 92%, about 93%, about 94%, about 95%, about 96%, about 97%, about 98%, about 99% and about 100% sequence identity to an amino acid sequence of SEQ ID NO: 11; and (c) CDR3 having any one of at least about 85%, about 86%, about 87%, about 88%, about 89%, about 90%, about 91%, about 92%, about 93%, about 94%, about 95%, about 96%, about 97%, about 98%, about 99% and about 100% sequence identity to an amino acid sequence selected of SEQ ID NO: 12. In some specific embodiments, provided is a BCMA-binding single variable domain comprising three CDRs (CDR1, CDR2 and CDR3), including: (a) CDR1 having any one of at least about 70%, about 75%, about 80%, about 85%, about 86%, about 87%, about 88%, about 89%, about 90%, about 91%, about 92%, about 93%, about 94%, about 95%, about 96%, about 97%, about 98%, about 99% and about 100% sequence identity to an amino acid sequence of SEQ ID NO: 13; (b) CDR2 having any one of at least about 85%, about 86%, about 87%, about 88%, about 89%, about 90%, about 91%, about 92%, about 93%, about 94%, about 95%, about 96%, about 97%, about 98%, about 99% and about 100% sequence identity to an amino acid sequence of SEQ ID NO: 14; and (c) CDR3 having any one of at least about 85%, about 86%, about 87%, about 88%, about 89%, about 90%, about 91%, about 92%, about 93%, about 94%, about 95%, about 96%, about 97%, about 98%, about 99% and about 100% sequence identity to an amino acid sequence selected of SEQ ID NO: 15. In some embodiments, a CDR having any one of at least about 70%, about 75%, about 80%, about 85%, about 86%, about 87%, about 88%, about 89%, about 90%, about 91%, about 92%, about 93%, about 94%, about 95%, about 96%, about 97%, about 98%, about 99% and about 100% sequence identity comprises substitutions (e.g., conservative substitutions), insertions or deletions compared to a reference sequence; however, single variable domains comprising the sequence retain the ability to bind to BCMA. In some embodiments, provided is a single variable domain comprising three CDRs (CDR1, CDR2 and CDR3), including: (a) CDR1 having any one of about 1 and about 2 amino acid substitutions (e.g., conservative substitutions), insertions or deletions compared to an amino acid sequence selected from the group consisting of SEQ ID NOs: 7, 10 and 13; (b) CDR2 having any one of about 1, about 2 and about 3 amino acid substitutions (e.g., conservative substitutions), insertions or deletions compared to an amino acid sequence selected from the group consisting of SEQ ID NOs: 8, 11 and 14; and (c) CDR3 having any one of about 1, about 2 and about 3 amino acid substitutions (e.g., conservative substitutions), insertions or deletions compared to an amino acid sequence selected from the group consisting of SEQ ID NOs: 9, 12 and 15. In some embodiments, the single variable domain is affinity-matured. In some embodiments, the single variable domain is derived from animals of the family Camelidae. In some embodiments, the single variable domain is humanized. In some embodiments, the single variable domain comprises an acceptor human framework.

In some embodiments, provided is a BCMA-binding single variable domain comprising three CDRs (CDR1, CDR2 and CDR3), including: CDR1 comprising an amino acid sequence of SEQ ID NO: 7; CDR2 comprising an amino acid sequence of SEQ ID NO: 8; and CDR3 comprising an amino acid sequence of SEQ ID NO: 9. In some embodiments, provided is a BCMA-binding single variable domain comprising three CDRs (CDR1, CDR2 and CDR3), including: CDR1 comprising an amino acid sequence of SEQ ID NO: 10: CDR2 comprising an amino acid sequence of SEQ ID NO: 11; and CDR3 comprising an amino acid sequence of SEQ ID NO: 12. In some embodiments, provided is a BCMA-binding single variable domain comprising three CDRs (CDR1, CDR2 and CDR3), including: CDR1 comprising an amino acid sequence of SEQ ID NO: 13; CDR2 comprising an amino acid sequence of SEQ ID NO: 14; and CDR3 comprising an amino acid sequence of SEQ ID NO: 15. In some embodiments, the single variable domain is derived from animals of the family Camelidae. In some embodiments, the single variable domain is humanized. In some embodiments, the single variable domain comprises an acceptor human framework.

In some embodiments, the single variable domain (including any of the embodiments described above, e.g., the single variable domain described above comprising particular CDR1, CDR2 and/or CDR3) comprises a $V_H$H having any one of at least about 85%, about 86%, about 87%, about 88%, about 89%, about 90%, about 91%, about 92%, about 93%, about 94%, about 95%, about 96%, about 97%, about 98%, about 99% and about 100% sequence identity to an amino acid sequence selected from the group consisting of SEQ ID NOs: 16, 18 and 20. In some specific embodiments, the single variable domain (including any of the embodiments described above, e.g., the single variable domain described above comprising particular CDR1, CDR2 and/or CDR3) comprises a $V_H$H having any one of at least about 85%, about 86%, about 87%, about 88%, about 89%, about 90%, about 91%, about 92%, about 93%, about 94%, about 95%, about 96%, about 97%, about 98%, about 99% and about 100% sequence identity to an amino acid sequence of SEQ ID NO: 16. In some specific embodiments, the single variable domain (including any of the embodiments described above, e.g., the single variable domain described above comprising particular CDR1, CDR2 and/or CDR3) comprises a $V_H$H having any one of at least about 85%, about 86%, about 87%, about 88%, about 89%, about 90%, about 91%, about 92%, about 93%, about 94%, about 95%, about 96%, about 97%, about 98%, about 99% and about 100% sequence identity to an amino acid sequence of SEQ ID NO: 18. In some specific embodiments, the single variable domain (including any of the embodiments described above, e.g., the single variable domain described above comprising particular CDR1, CDR2 and/or CDR3) comprises a $V_H$H domain having any one of at least about 85%, about 86%, about 87%, about 88%, about 89%, about 90%, about 91%, about 92%, about 93%, about 94%, about 95%, about 96%, about 97%, about 98%, about 99% and about 100% sequence identity to an amino acid sequence of SEQ ID NO: 20. In some more specific embodiments, the single variable domain comprises a $V_H$H having any one of at least about 85%, about 86%, about 87%, about 88%, about 89%, about 90%, about 91%, about 92%, about 93%, about 94%, about 95%, about 96%, about 97%, about 98%, about 99% and about 100% sequence identity to an amino acid sequence of SEQ ID NO: 16, and the $V_H$H comprises: CDR1 comprising an amino acid sequence of SEQ ID NO: 7, CDR2 comprising an amino acid sequence of SEQ ID NO: 8, and CDR3 comprising an amino acid sequence of SEQ ID NO: 9. In some more specific embodiments, the single variable domain comprises a $V_H$H having any one of at least about 85%, about 86%, about 87%, about 88%, about 89%, about 90%, about 91%, about 92%, about 93%, about 94%, about 95%, about 96%, about 97%, about 98%, about 99% and about 100% sequence identity to an amino acid sequence of SEQ ID NO: 18, and the $V_H$H comprises: CDR1 comprising an amino acid sequence of SEQ ID NO: 10, CDR2 comprising an amino acid sequence of SEQ ID NO: 11, and CDR3 comprising an amino acid sequence of SEQ ID NO: 12. In some more specific embodiments, the single variable domain comprises a $V_H$H having any one of at least about 85%, about 86%, about 87%, about 88%, about 89%, about 90%, about 91%, about 92%, about 93%, about 94%, about 95%, about 96%, about 97%, about 98%, about 99% and about 100% sequence identity to an amino acid sequence of SEQ ID NO: 20, and the V$_H$H comprises: CDR1 comprising an amino acid sequence of SEQ ID NO: 13, CDR2 comprising an amino acid sequence of SEQ ID NO: 14, and CDR3 comprising an amino acid sequence of SEQ ID NO: 15. In some embodiments, a V$_H$H sequence having any one of at least about 85%, about 86%, about 87%, about 88%, about 89%, about 90%, about 91%, about 92%, about 93%, about 94%, about 95%, about 96%, about 97%, about 98% and about 99% identity comprises substitutions (e.g., conservative substitutions), insertions or deletions compared to a reference sequence; however, single variable domains comprising the sequence retain the ability to bind to BCMA. In some embodiments, a total of 1-18, 1-16, 1-14, 1-12, 1-10, 1-9, 1-8, 1-7, 1-6, 1-5, 1-4, 1-3 or 1-2 amino acids are substituted, inserted and/or deleted in an amino acid sequence selected from the group consisting of SEQ ID NOs: 19, 21, 23 and 25. In some embodiments, the substitutions, insertions or deletions occur in regions outside of CDRs (i.e., in FRs). In some embodiments, the substitutions, insertions or deletions occur in CDR regions, for example, in one, two or three of CDR1, CDR2 and CDR3. In some embodiments, the substitutions, insertions or deletions occur in CDR regions and non-CDR regions. Optionally, the single variable domain comprises an amino acid sequence selected from the group consisting of SEQ ID NOs: 19, 21, 23 and 25, including post-translational modifications of the sequence.

In some embodiments, provided is an isolated single variable domain which is a V$_H$H comprising an amino acid sequence of SEQ ID NO: 16, 18 or 20.

In some embodiments, the single variable domain (including any of the embodiments described above, e.g., the single variable domain described above comprising particular CDR1, CDR2 and/or CDR3) is a V$_H$H. A basic V$_H$H has the following structure from N-terminus to C-terminus: FR1-CDR1-FR2-CDR2-FR3-CDR3-FR4, wherein FR1 to FR4 refer to framework regions 1 to 4, respectively, and wherein CDR1 to CDR3 refer to complementarity-determining regions 1 to 3. In some embodiments, the single variable domain (including any of the embodiments described above, e.g., the single variable domain described above comprising particular CDR1, CDR2 and/or CDR3) is a humanized VHH. A single variable domain of non-human origin may be "humanized" by replacing one or more amino acid residues in the amino acid sequence of the original single variable domain sequence with one or more amino acid residues present at corresponding positions in the VH domain of a human conventional four-chain antibody. Humanization may be desirable to reduce immunogenicity.

In some embodiments, the single variable domain according to any one of the embodiments described above may comprise one or several of the following properties and characteristics, alone or in combination:

(i) binding to human BCMA;

(ii) blocking binding of APRIL to BCMA; or (iii) not binding to human TACI or/and BAFFR proteins.

In some embodiments, the single variable domain binds to human BCMA.

In some embodiments, the single variable domain blocks binding of APRIL to BCMA.

In some embodiments, the single variable domain does not bind to human TACI or/and BAFFR proteins, exhibiting good specificity.

In some embodiments, the single variable domain combines the properties and characteristics (i)-(ii) described above. In some embodiments, the single variable domain combines the properties and characteristics (i) (iii) described above.

In some embodiments, the present invention provides a single variable domain that binds to the same epitope as any one of the single variable domains described herein. In some specific embodiments, provided is a single variable domain that binds to the same epitopes as a single variable domain comprising an amino acid sequence of SEQ ID NO: 16, 18 or 20. In some embodiments, the single variable domain that binds to the same epitopes is derived from animals of the family Camelidae or is humanized.

Based on the binding to the same epitopes, competitive screening of single variable domains can be carried out using conventional techniques known to those skilled in the art. For example, competitive and cross-competitive studies can be carried out to obtain single variable domains that compete with each other or cross-compete for binding to antigens. Thus, in some embodiments, the present invention provides a single variable domain that competes for binding to BCMA with any one of the single variable domains described herein. In some specific embodiments, provided is a single variable domain that competes for binding to BCMA with a single variable domain comprising an amino acid sequence of SEQ ID NO: 16, 18 or 20. The binding to BCMA can be measured by ELISA, flow cytometry or surface plasmon resonance (SPR) assay, or any other method known in the art. In some embodiments, the single variable domain that competes for binding to BCMA is derived from animals of the family Camelidae or is humanized.

The present invention provides some exemplary BCMA-binding single variable domains. The amino acid sequences of the CDRs (CDR1, CDR2 and CDR3) of the exemplary single variable domains provided herein are provided in Table S2 below. The full-length amino acid sequences of the exemplary single variable domains are provided in Table S3 below.

TABLE S2

| CDR sequences of single variable domains | | | |
|---|---|---|---|
| Name | CDR1 | CDR2 | CDR3 |
| 1A5 single variable domain | PCAMG (SEQ ID NO: 7) | WITVDGTTDYADSVKG (SEQ ID NO: 8) | VYILTPSCRPQP (SEQ ID NO: 9) |
| 1B5 single variable domain | SDCMG (SEQ ID NO: 10) | RIETGYGGTLYADSVKG (SEQ ID NO: 11) | KRSWCSPTWWREVDYNY (SEQ ID NO: 12) |

TABLE S2-continued

| CDR sequences of single variable domains | | | |
|---|---|---|---|
| Name | CDR1 | CDR2 | CDR3 |
| 1B11 single variable domain | MVCMG (SEQ ID NO: 13) | LITTDGGTTLYADSVKG (SEQ ID NO: 14) | DDRPWCMTVGVRTEDYDT (SEQ ID NO: 15) |

TABLE S3

| Full length sequences of single variable domains | | |
|---|---|---|
| Name | Amino acid sequence | SEQ ID NO: |
| 1A5 single variable domain | QVQLVESGGGSVQAGGSLLLSCAASGYTFSPCAM GWFRQAPGKERSLVSWITVDGTTDYADSVKGRFT ISRDNAKNMVYLQMTSLEPEDTATYYCNTVYILT PSCRPQPWGPGTQVTVSS | 16 |
| 1B5 single variable domain | QVQLVESGGGSVQAGGSLRLSCAASGVTFNSDCM GWFRQAPGKEREAVARIETGYGGTLYADSVKGRF TISRDNAKKTVYLQMNSLKFEDTAMYYCAAKRSW CSPTWWREVDYNYWGQGTLVTVSS | 18 |
| 1B11 single variable domain | QVQLVESGGGSVPAGGSMRLSCAASGYRNPMVCM GWFRQAPGKKREGVALITTDGGTTLYADSVKGRF TISQDNAKNTVYLQMNNLKPEDTAMYTCAADDRP WCMTVGVRTEDYDTWGQGTLVTVSS | 20 |

Antigen-Binding Molecule

The single variable domains of the present invention can be used to construct any desired antigen-binding molecule, thereby imparting to the antigen-binding molecule the property of targeted binding to BCMA or other properties of the single variable domains. Accordingly, the present invention provides an isolated antigen-binding molecule comprising at least one (one or more) single variable domain of the present invention.

In some embodiments, the antigen-binding molecule comprises at least one single variable domain comprising CDR1, CDR2 and CDR3 selected from any one of the following:

(i) CDR1 set forth in SEQ ID NO: 7, CDR2 set forth in SEQ ID NO: 8, and CDR3 set forth in SEQ ID NO: 9;

(ii) CDR1 set forth in SEQ ID NO: 10, CDR2 set forth in SEQ ID NO: 11, and CDR3 set forth in SEQ ID NO: 12; and (iii) CDR1 set forth in SEQ ID NO: 13, CDR2 set forth in SEQ ID NO: 14, and CDR3 set forth in SEQ ID NO: 15.

In some embodiments, the single variable domain comprises an amino acid sequence set forth in SEQ ID NO: 16, 18 or 20. In some more specific embodiments, the amino acid sequence of the single variable domain is set forth in SEQ ID NO: 16, 18 or 20.

When the antigen-binding molecule comprises two or more single variable domains, identical or different single variable domains may be selected.

The antigen-binding molecule includes antibodies, mono-specific antibodies, multispecific antibodies or immunoconjugates. In one embodiment, the antigen-binding molecule is an antibody. As a specific example, the antibody is a monospecific antibody. As another specific example, the antibody is a bispecific antibody. In one embodiment, the antibodies or immunoconjugates comprise an immunoglobulin constant region. In one more specific embodiment, the antibodies or immunoconjugates comprise a human immunoglobulin Fc. Preferably, the Fc is that of human IgG1, IgG2, IgG3 or IgG4.

In some embodiments, the antigen-binding molecule is derived from animals of the family Camelidae, is chimeric or is humanized.

In some embodiments, the antigen-binding molecule according to any one of the embodiments described above may comprise one or several of the following properties and characteristics, alone or in combination:

(i) binding to human BCMA;

(ii) blocking binding of APRIL to BCMA; or (iii) not binding to human TACI or/and BAFFR proteins.

In some embodiments, the antigen-binding molecule binds to human BCMA. In some embodiments, the antigen-binding molecule has the following binding affinity (KD) for human BCMA: in the range of about 1E-12 M to about 1E-08 M, about 1E-11 M to about 1E-09 M, or about 9.43E-11 M to about 1.21E-10 M. In some embodiments, the antigen-binding molecule has the following binding affinity (KD) for human BCMA: about 1E-08 M or less, about 1E-09 M or less, about 4.96E-10 M or less, about 1.21E-10 M or less, or about 9.43E-11 M or less. In some embodiments, the binding affinity KD of the antigen-binding molecule provided herein is measured by Biacore.

In some embodiments, the antigen-binding molecule blocks binding of APRIL to BCMA.

In some embodiments, the antigen-binding molecule does not bind to human TACI or/and BAFFR proteins, exhibiting good specificity.

In some embodiments, the antigen-binding molecule combines the properties and characteristics (i)-(ii) described above. In some embodiments, the antigen-binding molecule combines the properties and characteristics (i) (iii) described above.

The present invention provides exemplary antigen-binding molecules, such as monospecific antibodies (including 1A5-Fc, 1B5-Fc and 1B11-Fc antibodies). The single variable domain is fused with human IgG1, forming a homodimer through Fc. The amino acid sequences of the exemplary monospecific antibodies are provided in Table S4 below.

TABLE S4

| Full-length sequences of exemplary antigen-binding molecules | | |
|---|---|---|
| Name | Amino acid sequence | SEQ ID NO: |
| 1A5-Fc | QVQLVESGGGSVQAGGSLLLSCAASGYTFSPCAMGWFR QAPGKERSLVSWITVDGTTDYADSVKGRFTISRDNAKNM VYLQMTSLEPEDTATYYCNTVYILTPSCRPQPWGPGTQV TVSSEPKSCDKTHTCPPCPAPELLGGPSVFLFPPKPKDTL MISRTPEVTCVVVDVSHEDPEVKFNWYVDGVEVHNAKT KPREEQYNSTYRVVSVLTVLHQDWLNGKEYKCKVSNKA LPAPIEKTISKAKGQPREPQVYTLPPSRDELTKNQVSLTC | 22 |

TABLE S4-continued

Full-length sequences of exemplary antigen-
binding molecules

| Name | Amino acid sequence | SEQ ID NO: |
|---|---|---|
| | LVKGFYPSDIAVEWESNGQPENNYKTTPPVLDSDGSFFLY SKLTVDKSRWQQGNVFSCSVMHEALHNHYTQKSLSLSPG K | |
| 1B5-Fc | QVQLVESGGGSVQAGGSLRLSCAASGVTFNSDCMGWFR QAPGKEREAVARIETGYGGTLYADSVKGRFTISRDNAKK TVYLQMNSLKFEDTAMYYCAAKRSWCSPTWWREVDYN YWGQGTLVTVSSEPKSCDKTHTCPPCPAPELLGGPSVFLF PPKPKDTLMISRTPEVTCVVVDVSHEDPEVKFNWYVDGV EVHNAKTKPREEQYNSTYRVVSVLTVLHQDWLNGKEYK CKVSNKALPAPIEKTISKAKGQPREPQVYTLPPSRDELTK NQVSLTCLVKGFYPSDIAVEWESNGQPENNYKTTPPVLD SDGSFFLYSKLTVDKSRWQQGNVFSCSVMHEALHNHYT QKSLSLSPGK | 24 |
| 1B11-Fc | QVQLVESGGGSVPAGGSMRLSCAASGYRNPMVCMGWF RQAPGKKREGVALITTDGGTTLYADSVKGRFTISQDNAK NTVYLQMNNLKPEDTAMYTCAADDRPWCMTVGVRTED YDTWGQGTLVTVSSEPKSCDKTHTCPPCPAPELLGGPSV FLFPPPKPKDTLMISRTPEVTCVVVDVSHEDPEVKFNWYV DGVEVHNAKTKPREEQYNSTYRVVSVLTVLHQDWLNG KEYKCKVSNKALPAPIEKTISKAKGQPREPQVYTLPPSRD ELTKNQVSLTCLVKGFYPSDIAVEWESNGQPENNYKTTP PVLDSDGSFFLYSKLTVDKSRWQQGNVFSCSVMHEALH NHYTQKSLSLSPGK | 26 |

Composition

The present invention provides a pharmaceutical composition comprising an active ingredient and a pharmaceutically acceptable carrier, wherein the active ingredient is the single variable domain described herein or the antigen-binding molecule described herein. In some embodiments, any one or more of the 1A5-Fc, 1B5-Fc, and 1B11-Fc antibodies, and pharmaceutically acceptable carriers are formed into a pharmaceutical composition. The pharmaceutically acceptable carriers include, for example, excipients, diluents, encapsulating materials, fillers, buffers or other agents.

Isolated Nucleic Acid

The present invention provides an isolated nucleic acid encoding the single variable domain described herein or the antigen-binding molecule described herein. In some embodiments, the nucleic acid encodes a single variable domain, such as the single variable domains of 1A5-Fc, 1B5-Fc and 1B11-Fc. In some embodiments, the nucleic acid encodes an antigen-binding molecule, such as 1A5-Fc, 1B5-Fc and 1B11-Fc. By way of example, the nucleic acid sequences of some single variable domains, antigen-binding molecules are listed in the sequence listing.

Vector

The present invention provides a vector comprising the isolated nucleic acid described herein. In some embodiments, the vector described herein is a cloning vector; in some other embodiments, the vector described herein is an expression vector. The expression vector is optionally any expression vector capable of expressing the single variable domains or antigen-binding molecules described herein. As a specific example, the expression vector is pcDNA3.1.

Host Cell

In some embodiments, the present invention provides a host cell comprising the vector described herein, the host cell being a suitable host cell for cloning or expressing a single variable domain or an antigen-binding molecule. In some embodiments, the host cell is a prokaryotic cell. In other embodiments, the host cell is a eukaryotic cell. In some embodiments, the host cell is selected from the group consisting of yeast cells, mammalian cells or other cells suitable for preparing an antigen-binding molecule. Mammalian cells are, for example, Chinese hamster ovary (CHO) cells or CHO—S cells.

Method for Preparing Single Variable Domains or Antigen-Binding Molecules

In some embodiments, provided herein is a method for preparing a single variable domain, which comprises: culturing a host cell comprising a nucleic acid encoding the single variable domain described herein, and recovering the single variable domain from the host cell or host cell culture medium. In some embodiments, provided herein is a method for preparing an antigen-binding molecule, which comprises: culturing a host cell comprising a nucleic acid encoding the antigen-binding molecule described herein, and recovering the antigen-binding molecule from the host cell or host cell culture medium.

To produce the single variable domain or antigen-binding molecule, a nucleic acid encoding the single variable domain or antigen-binding molecule is inserted into a vector for further cloning and/or expression in a host cell. The nucleic acid can be obtained using various methods known in the art, such as gene splicing and chemical synthesis.

Use

The present invention provides use of single variable domains or antigen-binding molecules.

The present invention provides a method for treating a subject with a BCMA-expressing tumor, which comprises administering to the subject a therapeutically effective amount of the single variable domain described herein, the antigen-binding molecule described herein or the composition described herein. Subjects in need of treatment include those with a disease or condition, as well as those who may have the disease or condition and whose purpose is to prevent, delay or alleviate the disease or condition. The present invention also provides use of the single variable domain described herein, the antigen-binding molecule described herein or the composition described herein for manufacturing a medicament for treating a subject with a BCMA-expressing tumor.

The present invention provides a method for inhibiting, reducing or blocking BCMA signaling in a cell, which comprises administering to the cell an effective amount of the single variable domain described herein, the antigen-binding molecule described herein or the composition described herein. The present invention also provides use of a single variable domain or antigen-binding molecule for manufacturing a medicament for inhibiting, reducing or blocking BCMA signaling in a cell. In some embodiments, the cell is a tumor cell.

The present invention provides a method for killing BCMA-expressing tumor cells or inhibiting growth of BCMA-expressing tumor cells, which comprises contacting the tumor cells with the single variable domain described herein, the antigen-binding molecule described herein or the composition described herein. The present invention also provides use of the single variable domain, the antigen-binding molecule or the composition described herein for manufacturing a medicament for killing BCMA-expressing tumor cells or inhibiting growth of BCMA-expressing tumor cells.

The tumor described above may be a B-cell malignancy. A specific example is, e.g., lymphoma, myeloma, multiple myeloma or leukemia.

The present invention provides a method for treating a subject with an autoimmune disease, which comprises administering to the subject a therapeutically effective amount of the single variable domain described herein, the antigen-binding molecule described herein or the composition described herein. The present invention also provides use of the single variable domain described herein, the antigen-binding molecule described herein or the composition described herein for manufacturing a medicament for treating a subject with an autoimmune disease. The autoimmune disease may be systemic lupus erythematosus.

In some embodiments, provided is a method for detecting or measuring BCMA in a sample, which comprises contacting the sample with the single variable domain or the antigen-binding molecule described herein and detecting or measuring a binding complex.

Although the foregoing invention has been described in some detail by providing illustrations and examples for the purpose of clear understanding, it will be apparent to those of ordinary skill in the art in light of the teachings of the present invention that certain changes and modifications can be made to the present invention without departing from the spirit or scope of the appended claims. The following examples are provided for illustrative purposes only and are not intended to be limiting. Those skilled in the art will readily identify a variety of noncritical parameters that may be changed or modified to produce substantially similar results.

DETAILED DESCRIPTION

Example 1. Construction of Anti-BCMA Single-Domain Antibody Phage Display Library

1.1 Animal Immunization

A recombinant human BCMA-Fc fusion protein (ACRO, product catalog No. BC7-H5254) was mixed and emulsified with complete Freund's adjuvant in a ratio by volume of 1:1. A bactrian camel was first immunized by subcutaneous multipoint injection, and then immunized with the recombinant human BCMA-Fc fusion protein mixed and emulsified with incomplete Freund's adjuvant in a ratio by volume of 1:1 as a booster at intervals of 2 weeks. The serum was collected after the fourth or fifth immunization and assayed for anti-human BCMA antibody titer. After multiple rounds of immunization, the peripheral blood of the bactrian camel was collected, and peripheral blood mononuclear cells (PBMCs) were isolated.

1.2 RNA Extraction

The total RNA was extracted from the PBMCs (from 1.1) using TRIzol™ reagent. The quality of the extracted total RNA was assessed by 1% agarose gel electrophoresis. Quantification was performed by measuring absorbance at 260 nm and 280 nm. The ratio $OD_{260\ nm}/OD_{280\ nm}$ should fall somewhere between 1.8 and 2.0.

1.3 $V_HH$ Amplification

The total RNA was reverse-transcribed into cDNA using the cDNA synthesis kit PrimeScript™ II 1st Strand cDNA Synthesis Kit (TAKARA, product catalog No. 6210A) by following the instructions. The variable region ($V_HH$) sequence of the camel antibody was amplified by nested PCR, specifically as follows. With cDNA as a template, primers Call001 (SEQ ID NO: 1) and Call002 (SEQ ID NO: 2) were used to perform the first round of PCR amplification. The DNA product obtained in short fragments from the amplification was purified using a gel recovery kit (QIAGEN, product catalog No. 28706). With the product of the first round of PCR as a template, primers V-Back (SEQ ID NO: 3) and V-Fwd (SEQ ID NO: 4) were used to perform the second round of PCR amplification. The DNA product obtained from the amplification was the $V_HH$ coding fragment, which was then purified using a gel recovery kit (QIAGEN, product catalog No. 28706).

```
Call001 (SEQ ID NO: 1):
GTCCTGGCTGCTCTTCTACAAGG

Call002 (SEQ ID NO: 2):
GGTACGTGCTGTTGAACTGTTCC

V-Back (SEQ ID NO: 3):
GATGTGCAGCTGCAGGAGTCTGGRGGAGG

V-Fwd (SEQ ID NO: 4):
CTAGTGCGGCCGCTGAGGAGACGGTGACCTGGGT
```

The first round and the second round of PCR's program was as follows: pre-denaturation at 94° C. for 6 min, followed by denaturation at 94° C. for 30 s, annealing at 55° C. for 30 s, and extension at 72° C. for 30 s, for a total of 30 cycles of reaction, and finally, extension at 72° C. for 10 min.

1.4 Construction of $V_HH$ Phage Library

The $V_HH$ coding fragment obtained from the nested PCR amplification was digested with PstI/NotI endonuclease and inserted into a phagemid vector pMECS (NTCC Plasmid Vector, Strain, Cell and Gene Collection, product catalog No. pMECS) to construct a recombinant vector, which was then electrically transferred into *Escherichia coli* TG1 (Lucigen, product catalog No. 60502-1). A small portion of the transformed bacterial liquid was diluted and then applied to a selective plate containing 100 µg/mL ampicillin. The library capacity was calculated by colony counting, and 100 random clones were picked for sequencing to assess the library quality. The remaining bacterial liquid was applied to a selective plate containing 100 µg/mL ampicillin. The bacterial lawn of bacterial colonies were scraped off from the plate, supplemented with glycerol and cryopreserved at −80° C. as a library stock. The $V_HH$ library stock was amplified to logarithmic growth phase. Library amplification was performed by adding M13KO7 helper phages (New England Biolabs, product catalog No. NO315S), with shaking overnight at 200 rpm at 28° C. The bacterial liquid was centrifuged, and the supernatant was collected. ¼ supernatant volume of a PEG6000/NaCl solution (20% PEG6000 (w/v), 2.5 M NaCl) was added. The mixture was incubated on ice for 1-2 h to settle the phages and centrifuged. The settled phages were collected and resuspended in PBS, and then 20% glycerol was added. The suspension was preserved at −80° C. as a single-domain antibody phage display library.

Example 2. Anti-Human BCMA Single-Domain Antibody Screening

2.1 Panning

The single-domain antibody phage display library was subjected to solid-phase panning. The recombinant BCMA-Avitagen™ (ACRO, product catalog No. BCA-H82E4) was fixed on a high-adsorption microplate. After blocking, the phages obtained in 1.4 were added to the well plate, and the plate was incubated at 37° C. for 1-2 h. The plate was washed 10 times with phosphate-buffered saline with Tween (PBST) to remove non-specifically bound phage. After washing with PBS, the bound phages were eluted with trypsin enzyme. After the enzyme was neutralized with 4-(2-aminoethyl)benzenesulfonyl fluoride hydrochloride (AEBSF), the eluted phages were used to infect *Escherichia coli* TG1. After amplification, another round of library panning was carried out. After 2-3 rounds of panning and enrichment, the collected phages were used to infect *Escherichia coli* TG1 in logarithmic growth phase. The bacteria was applied to a selective plate containing 20% (w/v) glucose and 100 µg/mL ampicillin. Single clones were picked and cultured. Expression was induced by isopropyl-β-D-thiogalactoside (IPTG), and the supernatant was collected.

2.2 Positive Clone Identification

The picked clones were subjected to positive identification by indirect ELISA for human BCMA-His (ACRO, product catalog No. BCA-H522y). Human BCMA-His or a control protein human Fc protein (ACRO, product catalog No. FCC-H5214) was allowed to coat a high-adsorption microplate, and then the plate was blocked with a blocking buffer. The supernatant prepared in 2.1 was added, and the plate was incubated at 37° C. for 1 h. After the plate was washed, an HRP-conjugated anti-HA tag secondary antibody (GenScript, product catalog No. A01296) was added. The plate was incubated at 37° C. for 0.5 h and then washed 5 times, and a chromogenic substrate was added for color development. The light absorption signal values at the wavelength of 450 nm and the reference wavelength of 650 nm were measured. Positive clones that bind only to human BCMA-His with relatively high signal values were selected for preservation and sequenced. Positive clones 1A5, 1B5 and 1B11 were obtained from the screening. The sequence analysis showed that $V_H$H of 1A5 had a nucleotide sequence of SEQ ID NO: 17 and an amino acid sequence of SEQ ID NO: 16; $V_H$H of 1B5 had a nucleotide sequence of SEQ ID NO: 19 and an amino acid sequence of SEQ ID NO: 18; $V_H$H of 1B11 had a nucleotide sequence of SEQ ID NO: 21 and an amino acid sequence of SEQ ID NO: 20.

Example 3. Preparation of Anti-Human BCMA $V_H$H-Fc Chimeric Antibodies

3.1 Preparation of $V_H$H-Fc Chimeric Antibodies

The $V_H$H sequences of the positive clones obtained from the screening were linked to a human Fc region to construct $V_H$H-Fc chimeric antibodies. Specifically, the $V_H$H sequences sequenced in 2.2 were inserted into a pCDNA3.1 eukaryotic expression vector containing a human IgG1 constant region (the amino acid sequence was SEQ ID NO: 5). These $V_H$H-Fc chimeric antibodies were expressed using an Expifectamine™ CHO Transfection Kit transient expression system (Thermo Fisher Scientific Inc., product catalog No. A29129). After the antibodies were purified through a protein A affinity column, the binding activity of the $V_H$H-Fc chimeric antibodies to human BCMA protein was determined by indirect ELISA for human BCMA-His protein (see 3.2 for the method), and the binding of the antibodies to human TACI and BAFFR proteins was detected by surface plasmon resonance (see 3.3 for the method). The determination and detection showed that 1A5-Fc, 1B5 and 1B11-Fc were all able to specifically bind to human BCMA-His protein but did not bind to human TACI and BAFFR proteins. The amino acid sequence of full-length of 1A5-Fc is set forth in SEQ ID NO: 22, and the nucleotide sequence of full-length of 1A5-Fc is set forth in SEQ ID NO: 23. The amino acid sequence of full-length of 1B5-Fc is set forth in SEQ ID NO: 24, and the nucleotide sequence of full-length of 1B5-Fc is set forth in SEQ ID NO: 25. The amino acid sequence of full-length of 1B11-Fc is set forth in SEQ ID NO: 26, and the nucleotide sequence of full-length of 1B11-Fc is set forth in SEQ ID NO: 27.

Figure 1:
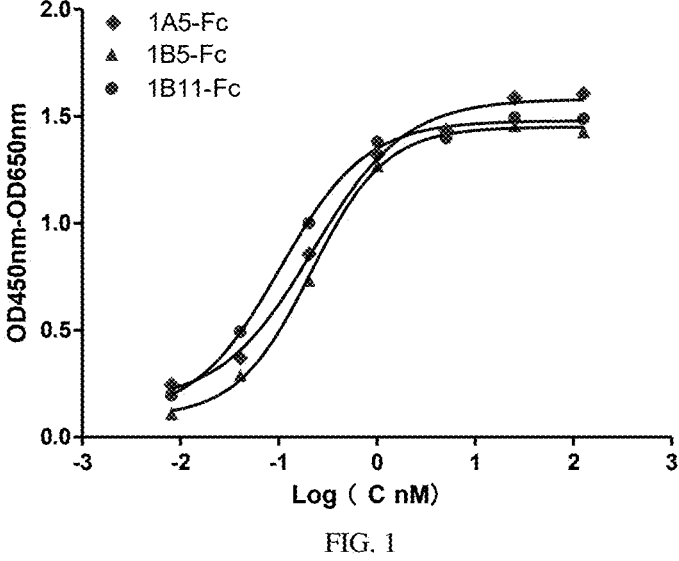
FIG. 1 shows curves of ELISA assays for binding of anti-human BCMA VHH-Fc chimeric antibodies to antigens.

3.2 Detection of Binding of Antibodies to Human BCMA-his Protein by Indirect ELISA 2 µg/mL human BCMA-His protein (ACRO, product catalog No. BCA-H522y) was allowed to coat a high-adsorption microplate, and then the plate was blocked with 3% (w/v) BSA blocking buffer. The anti-human BCMA $V_H$H-Fc chimeric antibodies (serially diluted 5-fold from the initial concentration of 126 nM to 7 concentrations) were added at 100 µL/well. The plate was incubated at 37° C. for 1 h. After the plated was washed, an HRP-conjugated anti-human IgG Fc tag secondary antibody (PerkinElmer, product catalog No. NEF802001EA) was added. The plate was incubated at 37° C. for 0.5 h and then washed 5 times, and a TMB substrate solution (TIANGEN, product catalog No. PA107) was added at 100 µL/well for color development. The light absorption signal values at the wavelength of 450 nm and the reference wavelength of 650 nm were measured. A curve (FIG. 1) was fit, and the $EC_{50}$ values (Table 1) were calculated.

TABLE 1

| Affinity of $V_H$H-Fc chimeric antibodies for human BCMA-His protein | |
| --- | --- |
| $V_H$H-Fc chimeric antibody | EC50(nM) |
| 1A5-Fc | 0.22 |
| 1B5-Fc | 0.21 |
| 1B11-Fc | 0.10 |

3.3 Detection of Binding of Antibodies to Human TACI and BAFFR Proteins by Surface Plasmon Resonance The anti-human BCMA VHH-Fc chimeric antibodies were tested for specificity using a biomolecular interaction analysis system (GE, Biacore T200). An anti-hIgG (Fc) antibody (GE, product catalog No. BR-1008-39) was amino-coupled to a CM5 sensor chip. The anti-human BCMA $V_H$H-Fc chimeric antibodies were diluted to 2 µg/mL with a running buffer (137 mM Nacl, 2.7 mM KCl, 10 mM $Na_2HPO_4·12H_2O$, 1.8 mM $KH_2PO_4$, 0.05% surfactant P-20 (w/v), pH 7.4), and capture was allowed for 90 s by passing the dilutions through experimental channels at a flow rate of 30 µL/min. Human TACI or BAFFR protein was diluted to 100 nM with the running buffer, and binding was allowed by passing the dilution at a flow rate of 50 µL/min. The binding signal curve was observed. No binding curve was observed for 1A5-Fc, 1B5-Fc or 1B11-Fc, which indicates that they do not bind to TACI and BAFFR proteins.

Example 4. Affinity of Anti-Human BCMA $V_H$H-Fc Chimeric Antibodies for Human BCMA

4.1 Determination of Affinity of Antibodies for Human BCMA by Surface Plasmon Resonance The anti-human BCMA $V_H$H-Fc chimeric antibodies were tested for affinity using a biomolecular interaction analysis system (GE, Biacore T200). An anti-hIgG (Fc) antibody (GE, product catalog No. BR-1008-39) was amino-coupled to a CM5 sensor chip. The anti-human BCMA $V_H$H-Fc chimeric antibodies were diluted to 1 µg/mL with a running buffer (137 mM Nacl, 2.7 mM KCl, 10 mM $Na_2HPO_4·12H_2O$, 1.8 mM $KH_2PO_4$, 0.05% surfactant P-20 (w/v), pH 7.4), and capture was allowed by passing the dilutions through experimental channels at a flow rate of 30 µL/min. Human BCMA-His (ACRO, product catalog No.

BCA-H522y) was diluted with the running buffer to 100 nM, 50 nM, 25 nM, 12.5 nmol/L, 6.25 nM and 3.125 nM, and binding was allowed for 200 s by passing the dilutions at a flow rate of 50 μL/min. Then dissociation was allowed for 800 s by stopping sample injection. The data signals were collected by BiaControl Software 2.0 in real time, and analyzed by BiaEvaluation Software 2.0. Fitting was performed using a Langmuir 1:1 model, and the binding rate constant Ka (1/Ms), the dissociation rate constant Kd (1/s) and the equilibrium constant KD (M) were calculated. The results are shown in Table 2. 1A5-Fc, 1B5-Fc and 1B11-Fc all have relatively high affinity for human BCMA protein. The assays showed that the KD of the chimeric control antibody BM-Fc (the sequence of the $V_HH$ control antibody (BM) was the same as SEQ ID NO: 125 in CN109153731A) was about 3E-10 M.

TABLE 2

Affinity of $V_HH$-Fc chimeric antibodies for human BCMA

| $V_HH$-Fc chimeric antibody | Ka(1/Ms) | Human BCMA-his Kd(1/s) | KD(M) |
|---|---|---|---|
| 1A5-Fc | 3.57E+06 | 4.32E−04 | 1.21E−10 |
| 1B5-Fc | 1.15E+06 | 5.72E−04 | 4.96E−10 |
| 1B11-Fc | 1.17E+06 | 1.10E−04 | 9.43E−11 |

4.2 Detection of Binding of Antibodies to Cells by Flow Cytometry

The binding of the anti-human BCMA $V_HH$-Fc chimeric antibodies to target cells with different BCMA expression levels was detected by flow cytometry. The CHO-hBCMA cells (iCarTab Biotechnology (Suzhou) Co. Ltd., product catalog No. AKD001A) were a stably transfected cell line highly expressing BCMA. The U266 cells (Cell Culture Center, Institute of Basic Medical Sciences, Chinese Academy of Medical Sciences, product catalog No. 3111C0001CCC000684) were a natural human myeloma cell line expressing BCMA at medium levels. The PRMI8226 cells (Cell Culture Center, Institute of Basic Medical Sciences, Chinese Academy of Medical Sciences, product catalog No. 3111C0001CCC000083) were a natural human myeloma cell line expressing BCMA at low levels. The HUVEC cells (ScienCell Research Laboratories, product catalog No. AKD001A 8000) were a human umbilical vein endothelial cell line not expressing BCMA. After $2×10^5$ target cells were incubated with a serially diluted anti-human BCMA $V_HH$-Fc chimeric antibodies (serially diluted 5-fold from the initial concentration of 126 nM to 6 concentrations) on ice for 1 h, the cells were washed. A PE-labeled anti-human IgG Fc antibody (Jackson Immuno Research, product catalog No. 109-116-170) was added, and the mixture was incubated on ice for 0.5 h. The cells were washed and then tested using a flow cytometer (Thermo Fisher Scientific Inc., Attune NXT).

As shown in FIGS. 2A-2C and Table 3, 1A5-Fc, 1B5-Fc and 1B11-Fc could all effectively bind to CHO-hBCMA cells that expressed BCMA at relatively high levels and U266 cells that expressed BCMA at medium levels; they also bound significantly to RPMI8226 cells that expressed BCMA at relatively low levels. As shown in FIG. 2D, 1A5-Fc, 1B5-Fc and 1B11-Fc did not bind significantly to HUVEC cells that did not express BCMA. The assays showed that the binding $EC_{50}$ of the chimeric control antibody BM-Fc (the sequence of the $V_HH$ control antibody (BM) was the same as SEQ ID NO: 125 in CN109153731A) was about 4 nM to CHO-hBCMA cells, and about 6 nM to U266 cells.

TABLE 3

Affinity of anti-human BCMA $V_HH$-Fc chimeric antibodies for target cells

| $V_HH$-Fc chimeric antibody | CHO-hBCMA cells EC50(nM) | U266 cells EC50(nM) |
|---|---|---|
| 1A5-Fc | 1.76 | 3.86 |
| 1B5-Fc | 1.91 | 2.58 |
| 1B11-Fc | 3.39 | 3.82 |

Example 5. Anti-Human BCMA $V_HH$-Fc Chimeric Antibodies Block Binding of APRIL to BCMA After serially diluted anti-human BCMA $V_HH$-Fc chimeric antibodies 1A5-Fc, 1B5-Fc and 1B11-Fc (serially diluted 5-fold from the initial concentration of 252 nM to 7 concentrations) were each mixed with 100 ng/mL biotin-conjugated recombinant BCMA-His protein (ACRO, product catalog No. BCA-H522y) in a ratio by volume of 1:1 and incubated at room temperature for 1 h, the mixtures were added to a microplate where a recombinant APRIL protein (ACRO, product catalog No. APL-H5244) was fixed, and meanwhile a control group with only 50 ng/ml biotin-conjugated recombinant BCMA-His proteinadded was set. The plate was incubated at 37° C. for 1 h and then washed to remove unbound biotin-conjugated recombinant BCMA-His protein. HRP-conjugated streptavidin (eBioscience, product catalog No. 18-4100-51) was added, and the plate was washed 5 times and then subjected to color development. The light absorption signal values at the wavelength of 450 nm and the reference wavelength of 650 nm were measured. The binding amount of BCMA to APRIL was calculated for each concentration of each antibody sample according to the formula binding amount=signal value of sample/signal value of control group×100%, and a curve was fit. As shown in FIG. 3 and Table 4, 1A5-Fc, 1B5-Fc, and 1B11-Fc could all effectively block the binding of APRIL to BCMA.

FIG. 4A shows the amino acid sequence of the extracellular region of human BCMA. FIG. 4B shows the structure of the extracellular region of human BCMA in the PDB database (PDB No. 2kn1). As shown in FIGS. 4A and 4B, human BCMA contains 3 pairs of disulfide bonds in the extracellular region: Cys8-Cys21, Cys24-Cys37 and Cys28-Cys41; APRIL mostly binds to the β-hairpin structure of human BCMA (Bossen, C. et al. Semin. Immunol. 2006, 18 (5): 263-275), therefore, the epitopes of clones 1A5-Fc, 1B5-Fc and 1B11-Fc are presumed to be located at Ser9-Pro23.

TABLE 4

Anti-human BCMA $V_HH$-Fc blocks binding of APRIL to BCMA

| $V_HH$-Fc chimeric antibody | IC50(nM) |
|---|---|
| 1A5-Fc | 0.21 |
| 1B5-Fc | 0.38 |
| 1B11-Fc | 0.41 |

Example 6. Epitope Difference Analysis Between Different Clones of Anti-Human BCMA $V_HH$ 6.1 Investigation of Competitive Relationships Between Different Clones of Anti-Human BCMA $V_HH$ by ELISA (Chessboard Method)

The human BCMA $V_HH$-Fc chimeric antibodies were diluted to 2 μg/mL and allowed to coat a high-adsorption microplate. The plate was washed and then blocked. 20 μg/mL human BCMA $V_HH$-Fc antibodies were incubated with a biotin-conjugated BCMA-His protein (ACRO, product catalog No. BCA-H522y) at room temperature for 0.5 h to give mixtures of antigen and antibody. According to a chessboard arrangement, the incubated mixtures of antigen and antibody or the biotin-conjugated BCMA-His protein alone (control) were added in sequence to the well plate at 100 μL/well. The plate was incubated at 37° C. for 1 h. The plate was washed to remove unbound biotin-conjugated recombinant BCMA-His protein. HRP-conjugated streptavidin (eBioscience, product catalog No. 18-4100-51) was added, and the plate was washed 5 times and then subjected to color development. The light absorption signal values at the wavelength of 450 nm and the reference wavelength of 650 nm were measured. The blocking rate of one antibody for the binding signal of another antibody to BCMA-Bio was calculated according to the formula blocking rate= core T200). An anti-His antibody (GE, product catalog No. 28995056) was amino-coupled to a CM5 sensor chip. A BCMA-His protein (ACRO, product catalog No. BCA-H522y) was diluted with a running buffer to about 1 μg/mL, and capture was allowed by passing the dilution through an experimental channel at a flow rate of 30 μL/min. The capture signal was controlled at 170-180 RU by adjusting the binding time. The anti-human BCMA $V_HH$-Fc chimeric antibody $V_HH$-Fc1 was diluted to 10 μg/mL (saturation concentration; the binding signal value remained unchanged after the concentration was increased) with the running buffer and injected until signals reached a plateau. Upon completion of the injection, another anti-human BCMA $V_HH$-Fc chimeric antibody $V_HH$-Fc2 was injected. The antibody binding curves were observed and the binding signal values for both antibodies were recorded separately. Changes in the signal values were shown in Table 6. The signal value for the saturated binding of 1B5-Fc antibody to BCMA was 613.3 RU. At this time, 1B11-Fc was injected, and the saturated signal value was 426.3 RU, which is comparable to the saturated signal value of 491.0 RU when 1B11-Fc was injected alone. Vice versa, and the positive and negative injection orders resulted into comparable cumulative signal values, which indicates that 1B5-Fc and 1B11-Fc could bind to different epitopes of BCMA protein simultaneously.

TABLE 6

| Changes in SPR signal values of VHH-Fc antibodies and analysis | | | | | | |
|---|---|---|---|---|---|---|
| | BCMA capture signal (RU) | VHH-Fc1 | VHH-Fc2 | VHH-Fc1 binding signal (RU) | VHH-Fc2 binding signal (RU) | Cumulative signal value (RU) |
| RUN1 | 172.0 | 1B5-Fc | 1B11-Fc | 613.3 | 426.3 | 1039.6 |
| RUN2 | 174.1 | 1B11-Fc | 1B5-Fc | 491.0 | 565.0 | 1056.0 |

(signal value of control group-signal value of sample group)/ signal value of control group×100%. The results are shown in Table 5. Positive control groups in which antibodies competed with themselves are shown on the diagonal line "\" of the chessboard (indicated in gray), and the blocking rates were over 95%. The blocking rate of 1B5-Fc for the binding of 1B11-Fc to human BCMA (12.6%) was less than 50%, and so was the blocking rate of 1B11-Fc for the binding of 1B5-Fc to human BCMA (14.5%), which indicates that there was no significant competitive relationship between 1B5-Fc and 1B11-Fc and that 1B5-Fc and 1B11-Fc could bind to different epitopes of BCMA protein simultaneously. The mutual blocking rate of 1A5-Fc and 1B11-Fc, and that of 1A5-Fc and 1B5-Fc are all over 85%.

TABLE 5

| ELISA (chessboard method) epitope competition | | | |
|---|---|---|---|
| Chessboard method | 1A5-Fc | 1B5-Fc | 1B11-Fc |
| 1A5-Fc | 99.1% | 99.9% | 103.6% |
| 1B5-Fc | 95.2% | 98.1% | 12.6% |
| 1B11-Fc | 87.2% | 14.5% | 97.0% |

6.2 Epitope Difference Analysis by Surface Plasmon Resonance

Epitope competition relationship analysis was performed using a biomolecular interaction analysis system (GE, Bia- 6.3 Epitope Difference Analysis by Flow Cytometry As the BCMA protein expressed on cell membranes may differ from free protein in effective exposure of epitopes, whether the two clones 1B5 and 1B11 can bind to the BCMA protein on cell membranes simultaneously was further determined by flow cytometry. The target cells were U266 cells. 20 μg/mL or 10 μg/mL 1B5-Fc and 1B11-Fc antibodies were each used to incubate $2×10^5$ target cells; or 20 μg/mL 1B5-Fc antibody was mixed with 20 μg/mL 1B11-Fc antibody in a ratio by volume of 1:1, and the mixture was used to incubate $2×10^5$ target cells. After being incubated on ice for 1 h, the cells were washed. A PE-labeled anti-human IgG Fc antibody (Jackson Immuno Research, product catalog No. 109-116-170) was added, and the mixture was incubated on ice for 0.5 h. The cells were washed and then tested using a flow cytometer (Thermo Fisher Scientific Inc., Attune NXT). The results are shown in Table 7. When 10 μg/mL identical antibody was added, the percent increase in the mean fluorescence value for the 1B5-Fc sample was 821.5/765.5−1=7.3%, and the percent increase in the mean fluorescence value for the 1B11-Fc sample was 975.0/947.0−1=2.9%, which indicates that the concentration at 10 μg/mL of both antibodies was close to a saturated concentration. Based on the above, 10 g/mL different antibody was added: when 10 μg/mL 1B11-Fc was added to 10 g/mL 1B5-Fc, the percent increase in the mean fluorescence value was 1505.0/765.5−1=96.6%; when 10 μg/mL 1B5-Fc was added to 10 μg/mL 1B11-Fc, the percent increase in the mean fluorescence value was 1505.0/947.0-1=58.9%, which indicates that 1B5-Fc and 1B11-Fc could bind to different epitopes of BCMA protein simultaneously.

The presumed epitope relationships of 1B5, 1B11 and 1B5 are shown in FIG. 4C: 1B5 and 1B11 each bind to a different epitope on human BCMA, whereas the epitopes on human BCMA to which 1A5 binds partially overlaps with the binding epitopes of 1B5 and 1B11.

TABLE 7

Binding of anti-human BCMA VHH chimeric antibodies to U266 cells

| No. | VHH-Fc chimeric antibodies | Mean fluorescence value (MFI) |
|---|---|---|
| a | 1B5-Fc, 10 μg/ml + 1B11-Fc, 10 μg/ml | 1505.0 |

TABLE 7-continued

Binding of anti-human BCMA VHH chimeric antibodies to U266 cells

| No. | VHH-Fc chimeric antibodies | Mean fluorescence value (MFI) |
|---|---|---|
| b | 1B5-Fc, 20 μg/ml | 821.5 |
| c | 1B11-Fc, 20 μg/ml | 975.0 |
| d | 1B5-Fc, 10 μg/ml | 765.5 |
| e | 1B11-Fc, 10 μg/ml | 947.0 |

The invention claimed is:

1. An isolated single variable domain that binds to BCMA, wherein the single variable domain comprises CDR1, CDR2 and CDR3 selected from any one of the following:
   (i) CDR1 comprising an amino acid sequence of SEQ ID NO: 7; CDR2 comprising an amino acid sequence of SEQ ID NO: 8; and CDR3 comprising an amino acid sequence of SEQ ID NO: 9;
   (ii) CDR1 comprising an amino acid sequence of SEQ ID NO: 10; CDR2 comprising an amino acid sequence of SEQ ID NO: 11; and CDR3 comprising an amino acid sequence of SEQ ID NO: 12; and
   (iii) CDR1 comprising an amino acid sequence of SEQ ID NO: 13; CDR2 comprising an amino acid sequence of SEQ ID NO: 14; and CDR3 comprising an amino acid sequence of SEQ ID NO: 15.

2. The isolated single variable domain according to claim 1, wherein the single variable domain comprises an amino acid sequence having at least 85% sequence identity to a sequence of SEQ ID NO: 16, 18 or 20; or the single variable domain comprises an amino acid sequence of SEQ ID NO: 16, 18 or 20.

3. The isolated single variable domain according to claim 1, wherein the single variable domain is derived from animals of the family Camelidae or is humanized.

4. The isolated single variable domain according to claim 1, wherein the single variable domain exhibits one of or a combination of several of the following properties:
   (i) binding to human BCMA;
   (ii) blocking binding of APRIL to BCMA; or
   (iii) not binding to human TACI or/and BAFFR proteins.

5. An isolated antigen-binding molecule that binds to BCMA and that comprises at least one single variable domain according to claim 1, wherein the antigen-binding molecule is an antibody, a monospecific antibody, a multispecific antibody or an immunoconjugate.

6. The isolated antigen-binding molecule according to claim 5, exhibiting one of or a combination of several of the following properties:
   (i) binding to human BCMA;
   (ii) blocking binding of APRIL to BCMA; and
   (iii) not binding to human TACI or/and BAFFR proteins.

7. A composition comprising an active ingredient and a pharmaceutically acceptable carrier, wherein the active ingredient is the antigen-binding molecule according to claim 5.

8. A method for treating a subject with a BCMA-expressing tumor or an autoimmune disease, comprising administering to the subject a therapeutically effective amount of the antigen-binding molecule according to claim 5.

9. The isolated single variable domain according to claim 3, wherein the single variable domain is a $V_H H$.

10. The isolated antigen-binding molecule according to claim 5, wherein the antibody or the immunoconjugate comprises an immunoglobulin constant region.

11. The isolated antigen-binding molecule according to claim 10, wherein the immunoglobulin constant region comprises a human immunoglobulin Fc.

12. The isolated antigen-binding molecule according to claim 11, wherein the Fc is an Fc of IgG1, IgG2, IgG3 or IgG4.

13. The isolated antigen-binding molecule according to claim 5, wherein the antigen-binding molecule comprises an amino acid sequence set forth in SEQ ID NO: 22, 24 or 26.

14. The method according to claim 8, wherein the tumor is a B-cell malignancy.

15. The method according to claim 14, wherein the B-cell malignancy is lymphoma, myeloma, multiple myeloma or leukemia.

16. The method according to claim 8, wherein the autoimmune disease is systemic lupus erythematosus.

* * * * *

```
SEQUENCE LISTING

<160> NUMBER OF SEQ ID NOS: 27

<210> SEQ ID NO 1
<211> LENGTH: 23
<212> TYPE: DNA
<213> ORGANISM: Artificial Sequence
<220> FEATURE:
<223> OTHER INFORMATION: Primer Sequence of Call001

<400> SEQUENCE: 1
gtcctggctg ctcttctaca agg                                           23

<210> SEQ ID NO 2
<211> LENGTH: 23
<212> TYPE: DNA
<213> ORGANISM: Artificial Sequence
<220> FEATURE:
<223> OTHER INFORMATION: Primer Sequence of Call002

<400> SEQUENCE: 2
ggtacgtgct gttgaactgt tcc                                           23

<210> SEQ ID NO 3
<211> LENGTH: 29
<212> TYPE: DNA
<213> ORGANISM: Artificial Sequence
<220> FEATURE:
<223> OTHER INFORMATION: Primer Sequence of V-Back

<400> SEQUENCE: 3
gatgtgcagc tgcaggagtc tggrggagg                                     29

<210> SEQ ID NO 4
<211> LENGTH: 34
<212> TYPE: DNA
<213> ORGANISM: Artificial Sequence
<220> FEATURE:
<223> OTHER INFORMATION: Primer Sequence of V-Fwd

<400> SEQUENCE: 4
ctagtgcggc cgctgaggag acggtgacct gggt                               34

<210> SEQ ID NO 5
<211> LENGTH: 232
<212> TYPE: PRT
<213> ORGANISM: Homo sapiens
```

-continued

```
<400> SEQUENCE: 5

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
            165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
            210                 215                 220

Ser Leu Ser Leu Ser Pro Gly Lys
225                 230

<210> SEQ ID NO 6
<211> LENGTH: 54
<212> TYPE: PRT
<213> ORGANISM: Homo sapiens

<400> SEQUENCE: 6

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
            35                  40                  45

Val Lys Gly Thr Asn Ala
    50

<210> SEQ ID NO 7
<211> LENGTH: 5
<212> TYPE: PRT
<213> ORGANISM: Camelus bactrianus

<400> SEQUENCE: 7

Pro Cys Ala Met Gly
1               5
```

-continued

```
<210> SEQ ID NO 8
<211> LENGTH: 16
<212> TYPE: PRT
<213> ORGANISM: Camelus bactrianus

<400> SEQUENCE: 8

Trp Ile Thr Val Asp Gly Thr Thr Asp Tyr Ala Asp Ser Val Lys Gly
1               5                   10                  15

<210> SEQ ID NO 9
<211> LENGTH: 12
<212> TYPE: PRT
<213> ORGANISM: Camelus bactrianus

<400> SEQUENCE: 9

Val Tyr Ile Leu Thr Pro Ser Cys Arg Pro Gln Pro
1               5                   10

<210> SEQ ID NO 10
<211> LENGTH: 5
<212> TYPE: PRT
<213> ORGANISM: Camelus bactrianus

<400> SEQUENCE: 10

Ser Asp Cys Met Gly
1               5

<210> SEQ ID NO 11
<211> LENGTH: 17
<212> TYPE: PRT
<213> ORGANISM: Camelus bactrianus

<400> SEQUENCE: 11

Arg Ile Glu Thr Gly Tyr Gly Gly Thr Leu Tyr Ala Asp Ser Val Lys
1               5                   10                  15

Gly

<210> SEQ ID NO 12
<211> LENGTH: 17
<212> TYPE: PRT
<213> ORGANISM: Camelus bactrianus

<400> SEQUENCE: 12

Lys Arg Ser Trp Cys Ser Pro Thr Trp Trp Arg Glu Val Asp Tyr Asn
1               5                   10                  15

Tyr

<210> SEQ ID NO 13
<211> LENGTH: 5
<212> TYPE: PRT
<213> ORGANISM: Camelus bactrianus

<400> SEQUENCE: 13

Met Val Cys Met Gly
1               5

<210> SEQ ID NO 14
<211> LENGTH: 17
<212> TYPE: PRT
<213> ORGANISM: Camelus bactrianus

<400> SEQUENCE: 14

Leu Ile Thr Thr Asp Gly Gly Thr Thr Leu Tyr Ala Asp Ser Val Lys
1               5                   10                  15
```

-continued

Gly

<210> SEQ ID NO 15
<211> LENGTH: 18
<212> TYPE: PRT
<213> ORGANISM: Camelus bactrianus

<400> SEQUENCE: 15

Asp Asp Arg Pro Trp Cys Met Thr Val Gly Val Arg Thr Glu Asp Tyr
1               5                   10                  15

Asp Thr

<210> SEQ ID NO 16
<211> LENGTH: 120
<212> TYPE: PRT
<213> ORGANISM: Camelus bactrianus

<400> SEQUENCE: 16

Gln Val Gln Leu Val Glu Ser Gly Gly Gly Ser Val Gln Ala Gly Gly
1               5                   10                  15

Ser Leu Leu Leu Ser Cys Ala Ala Ser Gly Tyr Thr Phe Ser Pro Cys
            20                  25                  30

Ala Met Gly Trp Phe Arg Gln Ala Pro Gly Lys Glu Arg Ser Leu Val
            35                  40                  45

Ser Trp Ile Thr Val Asp Gly Thr Thr Asp Tyr Ala Asp Ser Val Lys
        50                  55                  60

Gly Arg Phe Thr Ile Ser Arg Asp Asn Ala Lys Asn Met Val Tyr Leu
65                  70                  75                  80

Gln Met Thr Ser Leu Glu Pro Glu Asp Thr Ala Thr Tyr Tyr Cys Asn
                85                  90                  95

Thr Val Tyr Ile Leu Thr Pro Ser Cys Arg Pro Gln Pro Trp Gly Pro
            100                 105                 110

Gly Thr Gln Val Thr Val Ser Ser
        115                 120

<210> SEQ ID NO 17
<211> LENGTH: 360
<212> TYPE: DNA
<213> ORGANISM: Camelus bactrianus

<400> SEQUENCE: 17
caggtgcagc tggtggagtc tgggggaggc tcggtgcagg ctggagggtc tctattactc     60
tcctgtgcag cctctggata caccttcagt ccctgcgcca tgggctggtt ccgccaggct    120
ccagggaagg agcgctcgtt ggtctcatgg attactgttg atggtacaac agactatgca    180
gactccgtga agggccgatt caccatctcc cgagacaacg ccaagaacat ggtgtatctg    240
caaatgacta gtttggaacc tgaggacacg gccacgtatt actgtaatac tgtgtacatt    300
cttactccgt cctgccgccc ccagccctgg ggccggggga cccaggtcac tgtctcatca    360

<210> SEQ ID NO 18
<211> LENGTH: 126
<212> TYPE: PRT
<213> ORGANISM: Camelus bactrianus

<400> SEQUENCE: 18

Gln Val Gln Leu Val Glu Ser Gly Gly Gly Ser Val Gln Ala Gly Gly
1               5                   10                  15

```
Ser Leu Arg Leu Ser Cys Ala Ala Ser Gly Val Thr Phe Asn Ser Asp
            20                  25                  30

Cys Met Gly Trp Phe Arg Gln Ala Pro Gly Lys Glu Arg Glu Ala Val
            35                  40                  45

Ala Arg Ile Glu Thr Gly Tyr Gly Gly Thr Leu Tyr Ala Asp Ser Val
    50                  55                  60

Lys Gly Arg Phe Thr Ile Ser Arg Asp Asn Ala Lys Lys Thr Val Tyr
65                  70                  75                  80

Leu Gln Met Asn Ser Leu Lys Phe Glu Asp Thr Ala Met Tyr Tyr Cys
                85                  90                  95

Ala Ala Lys Arg Ser Trp Cys Ser Pro Thr Trp Trp Arg Glu Val Asp
            100                 105                 110

Tyr Asn Tyr Trp Gly Gln Gly Thr Leu Val Thr Val Ser Ser
        115                 120                 125
```

<210> SEQ ID NO 19
<211> LENGTH: 378
<212> TYPE: DNA
<213> ORGANISM: Camelus bactrianus

<400> SEQUENCE: 19

```
caggtgcagc tggtggagtc tgggggaggc tcggtgcagg ctggagggtc tctgagactc     60
tcctgtgcag cctctggagt cacttttaat agtgactgta tgggttggtt ccgccaggct    120
ccgggaaagg agcgcgaggc agtcgcacgt attgaaactg gttatggtgg cactctctat    180
gccgactccg tgaagggacg attcaccatc tcccgagaca cgccaagaa gacggtgtat    240 ctgcaaatga acagcctaaa atttgaggac actgccatgt actactgtgc ggctaagaga    300
tcctggtgtt ctcctacgtg gtggcgcgaa gttgactata actactgggg acaggggacc    360
ctggtcactg tctcatca                                                  378
```

<210> SEQ ID NO 20
<211> LENGTH: 127
<212> TYPE: PRT
<213> ORGANISM: Camelus bactrianus

<400> SEQUENCE: 20

```
Gln Val Gln Leu Val Glu Ser Gly Gly Gly Ser Val Pro Ala Gly Gly
1               5                   10                  15

Ser Met Arg Leu Ser Cys Ala Ala Ser Gly Tyr Arg Asn Pro Met Val
            20                  25                  30

Cys Met Gly Trp Phe Arg Gln Ala Pro Gly Lys Lys Arg Glu Gly Val
            35                  40                  45

Ala Leu Ile Thr Thr Asp Gly Gly Thr Thr Leu Tyr Ala Asp Ser Val
    50                  55                  60

Lys Gly Arg Phe Thr Ile Ser Gln Asp Asn Ala Lys Asn Thr Val Tyr
65                  70                  75                  80

Leu Gln Met Asn Asn Leu Lys Pro Glu Asp Thr Ala Met Tyr Thr Cys
                85                  90                  95

Ala Ala Asp Asp Arg Pro Trp Cys Met Thr Val Gly Val Arg Thr Glu
            100                 105                 110

Asp Tyr Asp Thr Trp Gly Gln Gly Thr Leu Val Thr Val Ser Ser
        115                 120                 125
```

<210> SEQ ID NO 21
<211> LENGTH: 381
<212> TYPE: DNA

<213> ORGANISM: Camelus bactrianus

<400> SEQUENCE: 21
caggtgcagc tggtggagtc tggggaggc tcggtgcctg ctggagggtc tatgagactc        60
tcctgtgcag cctctggtta caggaatcct atggtgtgta tgggctggtt tcgccaggct       120
ccagggaaga agcgcgaggg ggtcgcactt attactactg atggtggaac cacactctac       180
gccgactccg tgaagggccg attcaccatc tcccaagaca cgccaagaa cacggtgtat        240 ctgcaaatga caacctgaa accagaggac actgccatgt acacctgtgc ggcagacgac        300
cgtccctggt gtatgacggt tggtgtgagg acggaagact atgacacctg gggccagggg       360
accctggtca ctgtctcatc a                                                 381

<210> SEQ ID NO 22
<211> LENGTH: 352
<212> TYPE: PRT
<213> ORGANISM: Artificial Sequence
<220> FEATURE:
<223> OTHER INFORMATION: the amino acid sequence of full-length of
      1A5-Fc

<400> SEQUENCE: 22

Gln Val Gln Leu Val Glu Ser Gly Gly Gly Ser Val Gln Ala Gly Gly
1               5                   10                  15

Ser Leu Leu Leu Ser Cys Ala Ala Ser Gly Tyr Thr Phe Ser Pro Cys
            20                  25                  30

Ala Met Gly Trp Phe Arg Gln Ala Pro Gly Lys Glu Arg Ser Leu Val
        35                  40                  45

Ser Trp Ile Thr Val Asp Gly Thr Thr Asp Tyr Ala Asp Ser Val Lys
    50                  55                  60

Gly Arg Phe Thr Ile Ser Arg Asp Asn Ala Lys Asn Met Val Tyr Leu
65                  70                  75                  80

Gln Met Thr Ser Leu Glu Pro Glu Asp Thr Ala Thr Tyr Tyr Cys Asn
                85                  90                  95

Thr Val Tyr Ile Leu Thr Pro Ser Cys Arg Pro Gln Pro Trp Gly Pro
                100                 105                 110

Gly Thr Gln Val Thr Val Ser Ser Glu Pro Lys Ser Cys Asp Lys Thr
            115                 120                 125

His Thr Cys Pro Pro Cys Pro Ala Pro Glu Leu Leu Gly Gly Pro Ser
        130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser His Glu Asp Pro
                165                 170                 175

Glu Val Lys Phe Asn Trp Tyr Val Asp Gly Val Glu Val His Asn Ala
                180                 185                 190

Lys Thr Lys Pro Arg Glu Glu Gln Tyr Asn Ser Thr Tyr Arg Val Val
            195                 200                 205

Ser Val Leu Thr Val Leu His Gln Asp Trp Leu Asn Gly Lys Glu Tyr
        210                 215                 220

Lys Cys Lys Val Ser Asn Lys Ala Leu Pro Ala Pro Ile Glu Lys Thr
225                 230                 235                 240

Ile Ser Lys Ala Lys Gly Gln Pro Arg Glu Pro Gln Val Tyr Thr Leu
                245                 250                 255

Pro Pro Ser Arg Asp Glu Leu Thr Lys Asn Gln Val Ser Leu Thr Cys
                260                 265                 270

-continued

```
Leu Val Lys Gly Phe Tyr Pro Ser Asp Ile Ala Val Glu Trp Glu Ser
        275                 280                 285

Asn Gly Gln Pro Glu Asn Asn Tyr Lys Thr Thr Pro Pro Val Leu Asp
    290                 295                 300

Ser Asp Gly Ser Phe Phe Leu Tyr Ser Lys Leu Thr Val Asp Lys Ser
305                 310                 315                 320

Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Gly Lys
            340                 345                 350

<210> SEQ ID NO 23
<211> LENGTH: 1056
<212> TYPE: DNA
<213> ORGANISM: Artificial Sequence
<220> FEATURE:
<223> OTHER INFORMATION: the nucleotide sequence of full-length of
      1A5-Fc

<400> SEQUENCE: 23
caagtgcaac tggtggagtc tggaggcggt tccgtgcagg ccggcggctc cctgctcctg      60
tcctgcgccg cttccggcta caccttctct ccttgtgcca tgggctggtt ccggcaggct     120
cctggcaaag aaagatccct ggtgtcttgg atcaccgtgg atggcaccac cgattacgct     180
gactccgtga agggcagatt caccatctct agagacaacg ccaagaacat ggtgtacctg     240
cagatgacca gcctggaacc tgaggatacc gctacctact actgcaacac cgtgtacatc     300
ctgacaccta gctgccggcc tcaaccttgg ggacctggaa cacaggtaac cgtgtcgtcc     360
gagcccaagt cttgcgacaa gacccacacc tgtcctcctt gtcctgctcc ggaactgctg     420
ggcggcccct tccgtgtttct gtttcctcca aagcctaagg acacactgat gatcagccgg     480 accctgagg tgacctgcgt ggtcgtggat gtctctcacg aggatcctga ggtgaagttc     540
aactggtacg tggatggagt ggaagtgcat aacgctaaaa ccaagcctag agaagagcag     600
tacaactcca cctacagagt ggtgtccgtg ctgaccgtgc tgcaccagga ttggctgaac     660
ggcaaagagt acaagtgcaa ggtgtccaac aaggctctgc ctgccccctat cgagaagacc     720 atctccaagg ccaagggcca gcctcgggag cctcaagtgt acaccctgcc tccttctcgc     780
gacgagctga ccaagaacca ggtgtctctg acctgcctgg tgaaaggctt ctacccctcc     840
gacatcgccg tggaatggga gtccaatggc agcccgaga acaactacaa gaccaccccca     900 cctgtgctgg actctgatgg ctccttcttc ctgtactcca agctgaccgt ggacaagtcc     960
agatggcagc agggcaacgt gttctcctgt tctgtgatgc acgaggccct gcacaaccac    1020
tacacacaga gtccctgag cctgtctcct ggcaag                                 1056

<210> SEQ ID NO 24
<211> LENGTH: 358
<212> TYPE: PRT
<213> ORGANISM: Artificial Sequence
<220> FEATURE:
<223> OTHER INFORMATION: the amino acid sequence of full-length of
      1B5-Fc

<400> SEQUENCE: 24

Gln Val Gln Leu Val Glu Ser Gly Gly Gly Ser Val Gln Ala Gly Gly
1               5                   10                  15

Ser Leu Arg Leu Ser Cys Ala Ala Ser Gly Val Thr Phe Asn Ser Asp
            20                  25                  30
```

```
Cys Met Gly Trp Phe Arg Gln Ala Pro Gly Lys Glu Arg Glu Ala Val
    35              40              45
Ala Arg Ile Glu Thr Gly Tyr Gly Gly Thr Leu Tyr Ala Asp Ser Val
    50              55              60
Lys Gly Arg Phe Thr Ile Ser Arg Asp Asn Ala Lys Lys Thr Val Tyr
65              70              75              80
Leu Gln Met Asn Ser Leu Lys Phe Glu Asp Thr Ala Met Tyr Tyr Cys
                85              90              95
Ala Ala Lys Arg Ser Trp Cys Ser Pro Thr Trp Trp Arg Glu Val Asp
            100             105             110
Tyr Asn Tyr Trp Gly Gln Gly Thr Leu Val Thr Val Ser Ser Glu Pro
        115             120             125
Lys Ser Cys Asp Lys Thr His Thr Cys Pro Pro Cys Pro Ala Pro Glu
    130             135             140
Leu Leu Gly Gly Pro Ser Val Phe Leu Phe Pro Pro Lys Pro Lys Asp
145             150             155             160
Thr Leu Met Ile Ser Arg Thr Pro Glu Val Thr Cys Val Val Val Asp
                165             170             175
Val Ser His Glu Asp Pro Glu Val Lys Phe Asn Trp Tyr Val Asp Gly
            180             185             190
Val Glu Val His Asn Ala Lys Thr Lys Pro Arg Glu Glu Gln Tyr Asn
        195             200             205
Ser Thr Tyr Arg Val Val Ser Val Leu Thr Val Leu His Gln Asp Trp
    210             215             220
Leu Asn Gly Lys Glu Tyr Lys Cys Lys Val Ser Asn Lys Ala Leu Pro
225             230             235             240
Ala Pro Ile Glu Lys Thr Ile Ser Lys Ala Lys Gly Gln Pro Arg Glu
                245             250             255
Pro Gln Val Tyr Thr Leu Pro Pro Ser Arg Asp Glu Leu Thr Lys Asn
            260             265             270
Gln Val Ser Leu Thr Cys Leu Val Lys Gly Phe Tyr Pro Ser Asp Ile
        275             280             285
Ala Val Glu Trp Glu Ser Asn Gly Gln Pro Glu Asn Asn Tyr Lys Thr
    290             295             300
Thr Pro Pro Val Leu Asp Ser Asp Gly Ser Phe Phe Leu Tyr Ser Lys
305             310             315             320
Leu Thr Val Asp Lys Ser Arg Trp Gln Gln Gly Asn Val Phe Ser Cys
                325             330             335
Ser Val Met His Glu Ala Leu His Asn His Tyr Thr Gln Lys Ser Leu
            340             345             350
Ser Leu Ser Pro Gly Lys
            355
```

<210> SEQ ID NO 25
<211> LENGTH: 1074
<212> TYPE: DNA
<213> ORGANISM: Artificial Sequence
<220> FEATURE:
<223> OTHER INFORMATION: the nucleotide sequence of full-length of
     1B5-Fc

<400> SEQUENCE: 25

```
caggtgcagt tggttgaatc tggcggcgga tctgtgcagg ctggcggatc tctgagactg       60
tcctgtgccg cttccggcgt caccttcaac tccgactgca tgggatggtt cagacaggcc      120
```

-continued

```
cctggcaaag agagagaggc cgtcgctagg atcgagaccg gctatggcgg aaccctgtac      180
gccgactccg tcaagggcag gttcaccatc agcagagaca acgccaagaa gaccgtgtac      240
ctgcagatga actccctgaa gttcgaggac accgccatgt actactgtgc tgccaagaga      300
agctggtgca gccctacctg gtggagagag gtggactaca actactgggg ccagggcaca      360
ctggtcaccg tgtcctctga gcctaagtcc tgcgacaaga cccacacctg tcctccatgt      420
cctgctccag aactgctcgg cggaccttcc gtgttcctgt ttcctccaaa gcctaaggat      480
accctgatga tctctcggac ccctgaagtg acctgcgtgg tggtggatgt gtctcacgag      540
gatcccgaag tgaagttcaa ttggtacgtg gacggcgtgg aagtgcacaa tgctaagacc      600
aagcctagag aggaacagta caactccacc tatagagtgg tgtccgtgct gaccgtgctg      660
caccaggatt ggctgaacgg caaagagtac aagtgcaagg tgtccaacaa ggccctgcct      720
gctcctatcg aaaagaccat ctccaaggcc aagggccagc ctagggaacc ccaggtttac      780
accttgcctc catctcggga cgagctgacc aagaaccagg tgtccctgac ctgtctggtc      840
aagggcttct acccctccga tatcgccgtg gaatgggagt ctaatggcca gccagagaac      900
aactacaaga caccccctcc tgtgctggac tccgacggct cattcttcct gtactccaag      960
ctgacagtgg acaagtccag atggcagcag ggcaacgtgt tctcctgctc cgtgatgcac     1020
gaggccctgc acaatcacta cacccagaag tccctgtctc tgagccccgg caaa           1074
```

```
<210> SEQ ID NO 26
<211> LENGTH: 359
<212> TYPE: PRT
<213> ORGANISM: Artificial Sequence
<220> FEATURE:
<223> OTHER INFORMATION: the amino acid sequence of full-length of
      1B11-Fc

<400> SEQUENCE: 26

Gln Val Gln Leu Val Glu Ser Gly Gly Gly Ser Val Pro Ala Gly Gly
1               5                   10                  15

Ser Met Arg Leu Ser Cys Ala Ala Ser Gly Tyr Arg Asn Pro Met Val
                20                  25                  30

Cys Met Gly Trp Phe Arg Gln Ala Pro Gly Lys Lys Arg Glu Gly Val
            35                  40                  45

Ala Leu Ile Thr Thr Asp Gly Gly Thr Thr Leu Tyr Ala Asp Ser Val
        50                  55                  60

Lys Gly Arg Phe Thr Ile Ser Gln Asp Asn Ala Lys Asn Thr Val Tyr
65                  70                  75                  80

Leu Gln Met Asn Asn Leu Lys Pro Glu Asp Thr Ala Met Tyr Thr Cys
                85                  90                  95

Ala Ala Asp Asp Arg Pro Trp Cys Met Thr Val Gly Val Arg Thr Glu
            100                 105                 110

Asp Tyr Asp Thr Trp Gly Gln Gly Thr Leu Val Thr Val Ser Ser Glu
        115                 120                 125

Pro Lys Ser Cys Asp Lys Thr His Thr Cys Pro Pro Cys Pro Ala Pro
        130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190
```

-continued

```
Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
        210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Asp Glu Leu Thr Lys
                260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
        290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
                340                 345                 350

Leu Ser Leu Ser Pro Gly Lys
        355
```

```
<210> SEQ ID NO 27
<211> LENGTH: 1077
<212> TYPE: DNA
<213> ORGANISM: Artificial Sequence
<220> FEATURE:
<223> OTHER INFORMATION: the nucleotide sequence of full-length of
      1B11-Fc

<400> SEQUENCE: 27
caggtgcagt tggttgaatc tggcggcgga tctgtgcccg ctggcggatc tatgagactg       60
tcctgtgccg cttccggcta cagaaacccc atggtctgca tgggctggtt cagacaggcc      120
cctggcaaga agagagaagg cgtcgccctg atcaccaccg atggcggaac aacattgtac      180
gccgactccg tcaagggcag gttcaccatc agccaggaca cgccaagaa caccgtgtac      240 ctgcagatga caatctgaa gcccgaggac accgccatgt acacctgtgc cgccgacgac      300
agaccttggt gtatgaccgt gggcgtcaga accgaggact acgacacatg gggccaggga      360
acactggtca ccgtgtcctc tgagcctaag tcctgcgaca gacccacac ctgtcctcca      420 tgtcctgctc cagaactgct cggcggacct tccgtgttcc tgtttcctcc aaagcctaag      480
gataccctga tgatctctcg gacccctgaa gtgacctgcg tggtggtgga tgtgtctcac      540
gaggatcccg aagtgaagtt caattggtac gtggacggcg tggaagtgca caatgctaag      600
accaagccta gagaggaaca gtacaactcc acctatagag tggtgtccgt gctgaccgtg      660
ctgcaccagg attggctgaa cggcaaagag tacaagtgca aggtgtccaa caaggccctg      720
cctgctccta tcgaaaagac catctccaag gccaagggcc agcctaggga accccaggtt      780
tacaccttgc ctccatctcg ggacgagctg accaagaacc aggtgtccct gacctgtctg      840
```

-continued

```
gtcaagggct tctacccctc cgatatcgcc gtggaatggg agtctaatgg ccagccagag      900
aacaactaca agacaacccc tcctgtgctg gactccgacg gctcattctt cctgtactcc      960
aagctgacag tggacaagtc cagatggcag cagggcaacg tgttctcctg ctccgtgatg     1020
cacgaggccc tgcacaatca ctacacccag aagtccctgt ctctgagccc cggcaaa       1077
```